(12) United States Patent
Khosla et al.

(10) Patent No.: US 8,153,593 B2
(45) Date of Patent: *Apr. 10, 2012

(54) TRANSGLUTAMINASE INHIBITORS AND METHODS OF USE THEREOF

(75) Inventors: Chaitan Khosla, Palo Alto, CA (US); Richard Edward Watts, Lindale, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/462,554

(22) Filed: Aug. 4, 2009

(65) Prior Publication Data

US 2009/0312272 A1 Dec. 17, 2009

Related U.S. Application Data

(63) Continuation of application No. 11/213,173, filed on Aug. 26, 2005, now Pat. No. 7,579,313, which is a continuation-in-part of application No. 10/716,846, filed on Nov. 18, 2003, now Pat. No. 7,265,093.

(51) Int. Cl.
*A61K 38/00* (2006.01)
*A61K 51/00* (2006.01)
*C07K 14/705* (2006.01)
*C07K 5/00* (2006.01)
*C07K 7/00* (2006.01)
*C07K 16/00* (2006.01)
*C07K 17/00* (2006.01)

(52) U.S. Cl. ........ 514/19.1; 514/1.1; 530/300; 424/1.69
(58) Field of Classification Search .................... None
See application file for complete search history.

(56) References Cited

U.S. PATENT DOCUMENTS

| | | | |
|---|---|---|---|
| 4,203,967 A | 5/1980 | Gallo-Torres | |
| 4,656,253 A | 4/1987 | Lewicki | |
| 4,912,120 A * | 3/1990 | Castelhano et al. | 514/380 |
| 4,929,630 A * | 5/1990 | Castelhano et al. | 514/380 |
| 5,208,021 A | 5/1993 | Johnson et al. | |
| 5,372,933 A | 12/1994 | Zamarron et al. | |
| 5,716,794 A | 2/1998 | Tjota | |
| 5,789,180 A | 8/1998 | Bernardin | |
| 5,817,523 A | 10/1998 | Picarelli | |
| 5,834,428 A | 11/1998 | Drucker | |
| 6,197,356 B1 | 3/2001 | Girsh | |
| 6,294,320 B1 | 9/2001 | Hrusa et al. | |
| 6,319,756 B2 | 11/2001 | Schuppan et al. | |
| 6,395,889 B1 | 5/2002 | Robison | |
| 6,410,550 B1 | 6/2002 | Coe et al. | |
| 6,667,160 B2 | 12/2003 | Fine | |
| 6,833,447 B1 | 12/2004 | Goldman et al. | |
| 6,903,246 B2 | 6/2005 | Gallie | |
| 6,962,989 B1 | 11/2005 | Pompejus et al. | |
| 7,144,569 B1 | 12/2006 | Anderson et al. | |
| 7,202,216 B2 | 4/2007 | Sollid et al. | |
| 7,265,093 B2 * | 9/2007 | Khosla et al. | 514/18.7 |
| 7,303,871 B2 | 12/2007 | Hausch et al. | |
| 7,320,788 B2 | 1/2008 | Shan et al. | |
| 7,462,688 B2 | 12/2008 | Khosla et al. | |
| 7,534,426 B2 | 5/2009 | Piper et al. | |
| 7,579,313 B2 * | 8/2009 | Khosla et al. | 514/1.1 |
| 7,605,150 B2 | 10/2009 | Khosla et al. | |
| 2001/0007690 A1 | 7/2001 | Girsh | |
| 2001/0036639 A1 | 11/2001 | Fine | |
| 2002/0039599 A1 | 4/2002 | Lin et al. | |
| 2002/0076834 A1 | 6/2002 | Detlef et al. | |
| 2003/0215438 A1 | 11/2003 | Hausch et al. | |
| 2003/0224476 A1 | 12/2003 | Chou | |
| 2004/0167069 A1 | 8/2004 | Khosla et al. | |
| 2004/0241664 A1 | 12/2004 | Dekker et al. | |
| 2005/0031603 A1 | 2/2005 | Hubertus de Jong et al. | |
| 2005/0049064 A1 | 3/2005 | Gagne | |
| 2005/0090653 A1 | 4/2005 | Klaveness et al. | |
| 2005/0244823 A1 | 11/2005 | Drijfhout et al. | |
| 2006/0052308 A1 | 3/2006 | Khosla et al. | |
| 2006/0178299 A1 | 8/2006 | Anderson et al. | |
| 2006/0240475 A1 | 10/2006 | Khosla et al. | |
| 2008/0299108 A1 | 12/2008 | Khosla et al. | |
| 2009/0156490 A1 | 6/2009 | Khosla et al. | |
| 2009/0220554 A1 | 9/2009 | Griffin et al. | |
| 2009/0304754 A1 | 12/2009 | Robic | |

FOREIGN PATENT DOCUMENTS

| | | |
|---|---|---|
| EP | 0 237 082 | 9/1987 |
| EP | 0 905 518 | 3/1999 |
| WO | 94/26774 | 11/1994 |
| WO | 1996010034 | 4/1996 |
| WO | 00/42213 | 7/2000 |
| WO | 01/25793 | 4/2001 |
| WO | 03/068170 | 8/2003 |
| WO | 03/096984 | 11/2003 |
| WO | 2003104273 | 12/2003 |
| WO | 2004/045392 | 6/204 |
| WO | 2005/049064 | 6/2005 |

OTHER PUBLICATIONS

Qiao; et al., "Antigen presentation to celiac lesion-derived T cells of a 33-mer gliadin peptide naturally formed by gastrointestinal digestion", Journal of Immunology (2004), 173(3):1757-1762.

Xia; et al., Equilibrium and kinetic analysis of the unusual binding behavior of a highly immunogenic gluten peptide to HLA-DQ2, Biochemistry (2005), 44(11):4442-4449.

Parrot; et al., "Circular dichroism and nuclear magnetic resonance spectroscopic analysis of immunogenic gluten peptides and their analogs", Journal of Biological Chemistry (2002), 277(47):45572-45578.

Schuppan; et al., "A Molecular Warhead and its Target Tissue Transglutaminase and Celiac Sprue", Chemistry & Biology (2003), 10(3):199-201.

Ahnen et al , Intestinal Aminooligopeptidase In Vivo Synthesis on Intracellualar Membranes of Rat Jejunum, J. Biol. Chem., (1982), 257: 12129-35.

(Continued)

*Primary Examiner* — Maury Audet
(74) *Attorney, Agent, or Firm* — Bozicevic, Field & Francis LLP; Pamela J. Sherwood

(57) ABSTRACT

Transglutaminase inhibitors and methods of use thereof are provided.

7 Claims, 7 Drawing Sheets
(2 of 7 Drawing Sheet(s) Filed in Color)

OTHER PUBLICATIONS

Arentz-Hansen et al. "Celiac Lesion T Cells Recognizes Epitopes that Cluster in Regions of Gliadins Rich in Proline Residues" Gastroenterology (2002), 123(3):803-809.

Arentz-Hansen et al., "The Intestinal T Cell Response to Gliadin in Adult Celiac Disease is Focused on a Single Deamidated Glutamine Targeted by Tissue Transglutaminase", J. Exp. Med. (2000), 191:603-12.

Bordusa et al. "The Specificity of Prolyl Endopeptidase From *Flavobacterium meningoseptum*: Mapping the S' Subsites by Positional Scanning Via ACYL Transfer", Bioorg. Med. Chem. (1998), 6:1775-80.

Castelhano et al., "Synthesis, Chemistry, and Absolute Configuratin of Novel Transglutaminiase Inhibitors Containing a 3-Halo-4,5-dihydroisoxazole1", Bioorg. Chem. (1988), 16:335-340.

Choi et al., "Chemistry and Biology of Dihydroisoxazole Derivatives: Selectives Inhibitors of Human Transglutaminase 2", Chem. & Biol. (2005), 12:469-475.

Colot et al. "The Genes Encoding Wheat Storage Proteins: Towards a Molecular Understanding of Bread-Making Quality and its Genetic Manipulation" Genet Eng, 1990, pp. 225-241, vol. 12.

Database Derwent, Acc-No. 1996-329479.

de Ritis G. et al. "In Vitro (organ culture) Studies of the Toxicity of Specific A-Gliadin Peptides in celiac Disease" Gastroenbterology, 1988, pp. 41-49, vol. 94.

Frazer et al. "Gluten-induced enteropathy: the effect of partially digested gluten." Lancet, Sep. 5, 1959, pp. 252-255, vol. 2.

Freund, K. et al. "Transglutaminase inhibition by 2-[(2-Oxopropyl)thio]imidazolium derivatives: mechanism of factor XIIIa inactivation" Biochemistry, 1994, pp. 10109-10119, vol. 33.

Greenberg, C., et al., "Transglutaminases: multifunctional cross-linking enzymes that stabilize tissues," FASEB J. (1991), 5:3071-3077.

Hausch et al., "Design, synthesis, and evaluation of gluten peptide analogs as selective inhibitors of human tissue transglutaminase", Chem Biol. (2003), 10(3):225-31.

Hitomi, K., et al., "GTP, an inhibitor of transglutaminases, is hydrolyzed by tissue-type transglutaminase (TGase 2) but not by epidermal-type transglutaminase (TGase 3)," Biosci. Biotechnol. Biochem. (2000), 64(3):657-659.

Kao Castle Pty LTD Sequence Analysis PCTRIS03104743, (2003).

Karpuj et al., "Prolonged survival and decreased abnormal movements in transgenic model of Huntington disease, with administration of the transglutaminase inhibitor cystamine", Nat Med. (2002), 8(2):143-9.

Keillor, Jeffrey W., "Tissue Transglutaminase Inhibition", Chem. & Biol. (2005) 12:410-412.

Kim et al., "Transglutaminases in disease", Neurochem. Int. (2002), 40:85-103.

Lahteenoja; et al., "Local Challenge on Oral Mucosa with an Gliadin Related Synthetic Peptide in Patients with Celiac Disease", Am. J. Gastroenterol. (2000), 95:2880.

Lion. *Flavobacterium meningosepticum*. Genbank Accession #/EMBL #: D10980. Aug. 1, 1992. http://www.infobiogen.fr/srs7lbin/cgi-bin/wgetz?-id+4jqa61Mc9PO+[uniprot-ID:PPCE_FLAME]+-e.

Lorand et al., "Novel inhibitors against the transglutaminase-catalysed crosslinking of lens proteins", Exp Eye Res. (1998), 66:531-6.

Martinet et al., "In vivo transglutaminase type 1 expression in normal lung, preinvasive bronchial lesions, and lung cancer", Am J Respir Cell Mol Biol. (2003), 28(4):428-35.

Messer et al. "Studies on the Mechanism of Destruction of the Toxic Action of Wheat Gluten in Coeliac Disease by Crude Papain" Gut., Aug. 1964, pp. 295-303, vol. 5.

Messer et al."Oral papain in gluten intolerance." Lancet, Nov. 6, 1976, p. 1022, vol. 2, Issue 7993.

Moodie, P. "Traditional Baking Enzymes-Proteases" Presented at the American Institute of Baking, Manhattan, Kansas, May 7, 2001 by Peter Moodie, Director—Sales & Marketing, Enzyme Development Corporation, Enzyme Development Corporation.

Online-Medical Dictionary. "Amino acid". http://cancerweb.ncl.ac.uk/cgi-bin/omd?query=amino+acid. Nov. 13, 1997.

Piper et al., "High selectivity of human tissue transglutaminase for immunoactive gliadin peptides: implications for celiac spure", Biochemistry, Jan. 8, 2002, pp. 386-393, vol. 41, Issue 1.

Piper, J., et al., "Effect of prolyl endopeptidase on digestive-resistant gliadin peptides in vivo," The Journal of Pharmacology and Experimental Therapeutics, 2004, pp. 213-219, vol. 311, Issue 1.

Sárdy, M., et al., "Epidermal transglutaminase (TGase 3) is the autoantigen of dermatitis herpetiformis,"(2002) J. Exp. Med., 195(6):747-757.

Schuppan, Detlef, "Special Reports and Reviews Current Concepts of Celiac Disease Pathogenesis", Gastroenterology, (2000), 119: 234-42.

Shan, L. et al. "Structural Basis for Gluten Intolerance in Celiac Sprue" Science 2002, pp. 2275-2279, vol. 297.

Shan, L. et al. "Comparative biochemical analysis of three bacterial prolyl endopeptidases: implications of coeliac sprue," Biochem J, 2004, pp. 311-318, vol. 383.

Sjostrom et al. "Identification of a Gliadin T-Cell Epitope in Coeliac Disease: General Importance of Gliadin Deamidation for Intestinal T-Cell Recognition" Scandinavian Journal of Immunology, Aug. 1998 , pp. 111-115(5), vol. 48, No. 2.

Stepniak, D. et al. "Highly efficient gluten degradation with a newly identified prolyl endoprotease: implications for celiac disease,"Am J Physiol Gastrointest Liver Physiol, 2006, pp. G621-G629, vol. 291.

Vader et al. "The Gluten Response in Children with Celiac Sprue Disease is Directed Toward Multiple Gliadin and Glutenin Peptides" Gastroenterology, 2002, pp. 1729-1737, vol. 122.

Vader et al. "The HLA-DQ2 Gene Dose Effect in Celiac Disease is Doirectly Related to the Magnitude and Breadth of Gluten-Specific T Cell Responses" PNAS, Oct. 14, 2003, pp. 12390-12395, vol. 123, No. 3.

Wieser, "The Precipitating Factor in Coeliac Disease", Baillieres Clinical Gastroenterol (1995), 9(2):191-207.

Yoshimoto et al., "Prolyl Endopeptidase From *Flavobacterium meningosepticum*: Cloning and Sequencing of the Enzyme Gene", J. Biochem. (1991), 110:873-8.

Zhang et al., "Identification of differentially expressed proteins in human glioblastoma cell lines and tumors", Glia (2003), 42(2):194-208.

Auger; et al., "Solid-State 13C NMR Study of a Transglutaminase-Inhibitor Adduct", Biochemistry (1993), 32:3930-3934.

Cornell; et al., "In vitro mucosal digestion of synthetic gliadin-derived peptides in celiac disease", Journal of Protein Chemistry (1995), 14(5):335-339.

Goldsmith; et al., "Inhibition of Human Epidermal Transglutaminases In-Vitro and In-Vitro by Tyrosineamidomethyldihydrohaloisoxazoles", Journal of Investigative Dermatology (1991), 97(1):156-158.

Killackey; et al., "A New Class of Mechanism-Based Inhibitors of Transglutaminase Enzymes Inhibits the Formation of Cross-Linked Envelopes by Human Malignant Keratinocytes", Molecular Pharmacology (1989), 35(5):701-706.

Smith; et al., "Abnormal expression of dipeptidylpeptidase IV activity in enterocyte brush-border membranes of children suffering from coeliac disease", Experimental Physiology (1990), 75(4):613-616.

Watts; et al., "Structure-activity relationship analysis of the selective inhibition of transglutaminase 2 by dihydroisoxazoles", Journal of Medicinal Chemistry (2006), 49(25):7493-7501.

Wruble, Milton, "Enteric Coatings. I. A Laboratory Method for the Study and Control of Enteric Coatings" Journal of the American Pharmaceutical Association (1935), XXIV(7):570-574.

Arentz-Hansen, et al., "Production of a Panel of Recombinant Gliadins for the Characterisation of T Cell Reactivity in Coeliac Disease" Gut. (2000), 46(1):46-51.

Bethune, et al. "Heterologous expression, purification, refolding, and structural-functionalcharacterization of EP-B2, a self-activating barley cysteine endoprotease," Chemistry & Biology (2006), 13:637-647.

Campbell, "Monoclonal Antibody Technology", Elsevier Science Publishers (1984), Section 1.3.4, pp. 1-32.

Garcia-Maroto, et al., "Nucleotide Sequence of a cDNA Encoding an Alpha/Beta-Type Gliadin from Hexaploid Wheat (*Triticum aestivum*)" Plant Molecular Biol. (1990), 14(5):867-868.

Hartmann, G., et al., "Rapid degradation of gliadin peptides toxic for coeliac disease patients by proteases from germinating cereals," Journal of Cereal Science (2006) 44:368-371.

Hausch et al., "Intestinal digestive resistance of immunodominant gliadin peptides", Am J Physl Gastrointest Liver Physiol (2002), 283:G996-G1003.

Nägele, et al. "Analysis of Food and Feed by way of Partial Sequences of Characteristic Protein Components (Leader Peptides)", Z Lebensm Unters Forsch (1991), 192:415-421.

Siegel; et al., "Transglutaminase 2 inhibitors and their therapeutic role in disease states", Pharmacology & Therapeutics (2007), 115:232-245.

Sturgess et al., "Wheat peptide challenge in coeliac disease", The Lancet (1994), 343:758-761.

Wiesner, "Relation Between Structure an Dcoeliac Toxicity" Acta Paediatr Suppl. (1996). 412:3-9.

* cited by examiner

```
                        SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Acylated proline
<220> FEATURE:
<221> NAME/KEY: MOD_RES
<222> LOCATION: (4)...(4)
<223> OTHER INFORMATION: 6-diazo-5-oxo-norleucine
<220> FEATURE:
<223> OTHER INFORMATION: Synthetic peptide

<400> SEQUENCE: 1

Pro Gln Pro Leu Leu Pro Phe
 1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)...(1)
<223> OTHER INFORMATION: acylated proline

<400> SEQUENCE: 2

Pro Glu Leu Pro Phe
 1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)...(1)
<223> OTHER INFORMATION: acylated proline
<220> FEATURE:
<221> NAME/KEY: MOD_RES
<222> LOCATION: (2)...(2)
<223> OTHER INFORMATION: 6-diazo-5-oxo-norleucine

<400> SEQUENCE: 3

Pro Leu Leu Pro Phe
 1               5
```

TRANSGLUTAMINASE INHIBITORS AND METHODS OF USE THEREOF

CROSS-REFERENCE TO RELATED APPLICATIONS

This application is a continuation of U.S. patent application Ser. No. 11/213,173, filed Aug. 26, 2005, which is a continuation in part of U.S. patent application Ser. No. 10/716,846, filed Nov. 18, 2003, all of which is herein specifically incorporated by reference.

FEDERALLY-SPONSORED RESEARCH OR DEVELOPMENT

This invention was made with Government support under contract DK063158 awarded by the National Institutes of Health. The Government has certain rights in this invention.

BACKGROUND OF THE INVENTION

Transglutaminases belong to a family of enzymes that play important roles in diverse biological functions by selectively cross-linking proteins. They catalyze formation of $\epsilon$-($\gamma$-glutamyl)-lysine cross-links between proteins, and may also incorporate polyamines into suitable protein substrates. This covalent isopeptide cross-link is stable and resistant to proteolysis, thereby increasing the resistance of tissue to chemical, enzymatic, and mechanical disruption. Among the members of this family are plasma transglutaminase, factor XIIIa, which stabilizes fibrin clots; keratinocyte transglutaminase and epidermal transglutaminase, which cross-link proteins on the outer surface of squamous epithelia; and tissue transglutaminase, which cross-links fibronectin in the extracellular matrix of organs such as brain, liver and the intestine.

Transglutaminase 2 (TG2, also known as tissue transglutaminase), a calcium-dependent member of the transglutaminase family, is reported to have extracellular as well as intracellular functions. Outside the cell TG2 plays a crucial role in shaping the extracellular matrix by cross-linking fibronectin and related proteins. TG2 also promotes cell adhesion and motility by forming non-covalent complexes with other key proteins such as integrins and fibronectin. Intracellular TG2 loses enzyme activity when bound to GTP, but functions as a G-protein in the phospholipase C signal transduction cascade. Human TG2 is a structurally and mechanistically complex protein. Its catalytic mechanism is similar to that employed by cysteine proteases, involving a catalytic triad of cysteine, histidine, and aspartate. The cysteine thiol group reacts with a glutamine sidechain of a protein substrate to form a reactive thioester intermediate, from which the acyl group is transferred to another amine substrate.

Several members of the transglutaminase family have been linked to disease, including tissue transglutaminase (TG2), and the skin transglutaminases, TG1 and TG3. TG2 is a cytoplasmic enzyme present in many cells, including those in the blood vessel wall. Aberrant TG2 activity is believed to play a role in neurological disorders such as Alzheimer's, Parkinson's and Huntington's disease (see, for example, Kim et al. (2002) Neurochem. Int. 40:85-103; Karpuj et al. (2002) Nature Med. 8, 143-149). In Celiac Sprue, where TG2 is the predominant autoantigen, its pivotal role in unmasking antigenic epitopes by site specific deamidation of gluten peptides is well established. Expression of TG1 and TG2 have been correlated with various types of malignancies (see Zhang et al. (2003) Glia 42:194-208; and Martinet et al. (2993) Am. J. Respir. Cell. Mol. Biol. 28, 428-435), including glioblastomas, lung and breast cancers, suggesting an important role for TG2 in tumor proliferation and survival. Taken together, the above findings make a strong case for suitable small molecule TG2 inhibitors as experimental therapeutic agents. The medicinal attractiveness of this protein target is underscored by the observation that TG2 knockout mice are normal, lacking developmental, physiological or reproductive defects.

Although a number of TG2 inhibitors have been used in biological studies over the past two decades, many of these compounds (e.g. monodansyl cadaverine) contain primary amines in addition to potential inhibitory motifs, and it remains unclear whether the observed effects are due to excess competing amines or by blockage of TG2 substrate turnover. A few studies have utilized a suicide inhibitor, L682777, which inhibits human TG2 (Lorand et al. (1998). Exp Eye Res. 66:531-6). However, L682777 was designed as a specific inhibitor of Factor XIIIa, and is therefore unsuitable for evaluating TG2 biology in vivo. More recently, mechanism-based active-site inhibitors of guinea pig and human (Hausch et al. (2003) Chem Biol 10, 225-231; Choi et al. (2005)Chem. Biol. 12, 469-475) TG2 have been reported.

In view of the serious and widespread nature of Celiac Sprue and the difficulty of removing gluten from the diet, better methods of treatment are of great interest. In particular, there is a need for treatment methods that allow the Celiac Sprue individual to eat gluten-containing foodstuffs without ill effect or at least to tolerate such foodstuffs in small or moderate quantities without inducing relapse. The present invention meets this need for better therapies for Celiac Sprue by providing new drugs and methods and formulations of new and existing drugs to treat Celiac Sprue. International Patent Application US03/04743, herein specifically incorporated by reference, discloses aspects of gluten protease stability and immunogenicity.

tTGase has also been implicated in certain cancers. Neurooncological diseases including malignant neoplasms such as glioblastomas and melanomas metastatic to the brain are notoriously resistant to standard radiation and chemotherapy treatment. Current treatment strategies generally fail to achieve long-term survival. Similarly certain benign CNS tumors such as meningiomas are resistant to chemotherapy and radiation. Current treatment strategies with these tumors typically require major surgical resections or treatment with radiation in an attempt to control growth of recurrent or non-resectable tumors. Meningiomas are generally resistant to radiation-induced cell death and to chemotherapy. The mechanisms responsible for the failure of these brain tumors to respond to chemotherapy and radiation are not known. Therefore, identification of agents that augment sensitivity to chemotherapy and radiation therapy is important for improving treatment strategies in patients with these and other refractory cancers.

SUMMARY OF THE INVENTION

The present invention provides methods that utilize administration of a transglutaminase inhibitor to a patient for the treatment of conditions associated with undesirable transglutaminase activity. The inhibition of tissue transglutaminase (tTGase; TG2) is of particular interest. tTGase inhibitors of interest include small molecule tTGase inhibitors comprising a 3-halo-4,5-dihydroisoxazole moiety.

In one embodiment, the present invention provides novel derivative compounds of 3-halo-4,5-dihydroisoxazoles and methods of treatment by administering those compounds. In another embodiment, the tTGase inhibitor employed in the method is an analog of isatin (2,3 diketoindoline).

In another embodiment, the invention provides pharmaceutical formulations comprising a tTGase inhibitor and a pharmaceutically acceptable carrier. In certain embodiments, the formulation also comprises one or more glutenases, as described in U.S. Provisional Application 60/392,782 filed Jun. 28, 2002; and U.S. Provisional Application 60/428,033, filed Nov. 20, 2002, both of which are incorporated herein by reference. In other embodiments, the formulation comprises a chemotherapeutic agent.

The invention also provides methods for the administration of enteric formulations of one or more tTGase inhibitors to treat Celiac Sprue.

In another aspect, the tTGase inhibitors and/or pharmaceutical formulations of the present invention are useful in treating cancer, including neurologic cancers, such as gliomas, astrocytomas, meningiomas (which are cancers of neural crest-derived cells), etc., and other cancers, including melanoma, as well as other neurological disorders including Alzheimer's and Huntington's diseases, where the TGases appear to be a factor in the formation of inappropriate proteinaceous aggregates. The tTGase inhibitors act on some cancers to sensitize the tumor cells to killing by chemotherapeutic agents and/or radiation.

These and other aspects and embodiments of the invention and methods for making and using the invention are described in more detail in the description of the drawings and the invention, the examples, the claims, and the drawings that follow.

BRIEF DESCRIPTION OF THE DRAWINGS

The patent application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
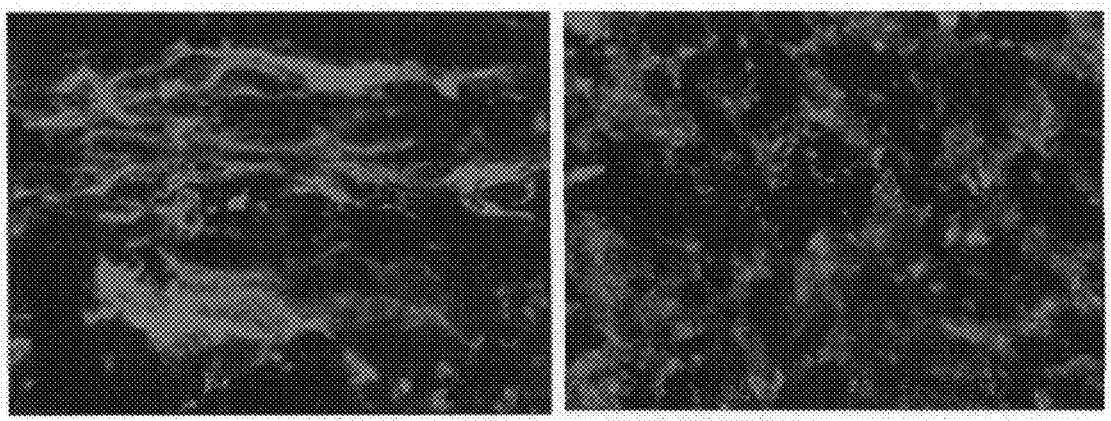
FIG. 1: Comparison of immunohistochemical staining of fibronectin in tumors from BCNU-treated mouse brains (right) and from mice treated with BCNU+35 mg/kg KCC009 (left).

Transglutaminase inhibitors of the invention are administered to a patient for the treatment of conditions associated with undesirable transglutaminase activity, including Celiac Sprue, dermatitis herpetiformis, cancer, and neurological disorders including Alzheimer's and Huntington's diseases.

In some embodiments, particularly for the treatment of Celiac Sprue, the compositions of the invention include formulations of tTGase inhibitors that comprise an enteric coating that allows delivery of the agents to the intestine in an active form; the agents are stabilized to resist digestion or alternative chemical transformations in acidic stomach conditions. In another embodiment, food is pretreated or combined with glutenase, or a glutenase is co-administered (whether in time or in a formulation of the invention) with a tTGase inhibitor of the invention.

For the treatment of cancer, the tTGase inhibitors can act as a sensitizing agent, which enhance killing by a second agent, e.g. radiation, cytotoxic drugs, and the like. For sensitization, the tTGase inhibitor may be administered separately or in a co-formulation with a cytotoxic agent. Although the cytotoxic agents can be active when administered alone, the concentrations required for a therapeutic dose may create undesirable side effects. The combination therapy may provide for a therapeutic effect with less toxicity.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. For example, treatment of a cancer patient may be reduction of tumor size, elimination of malignant cells, prevention of metastasis, or the prevention of relapse in a patient who has been cured.

Disease Conditions

A number of pathological conditions have been associated with undesirable activity of tissue transglutaminases. For the most part, the disease-associated transglutaminases of interest for the present invention are TG1, TG2, and TG3. Conditions may involve over-expression of the transglutaminase, expression of transglutaminase in tissues or sites where it is not normally expressed, or may involve normal expression of transglutaminase in a disease context.

Diseases associated with transglutaminase include, inter alia, celiac sprue; dermatitis herpetiformis; inclusion body myositis; atherosclerosis; Alzheimer's disease; Huntington's disease; Parkinson's disease; progressive supranuclear palsy; and tumors, e.g. glioblastomas, meningioma, melanoma, etc.

Celiac Sprue is characterized by damage to the upper small intestine, causing effacement of the villi to produce a characteristically flat mucosa with markedly hypertrophic crypts. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations. Therapeutic effect for Celiac Sprue is measured in terms of clinical outcome, or by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Also both the physician and patient can identify a reduction in symptoms of a disease. Evidence of therapeutic effect may be any diminution in the severity of disease, particularly diminution of the severity of such symptoms as fatigue, chronic diarrhea, malabsorption of nutrients, weight loss, abdominal distension, and anemia. Other disease indicia include the presence of antibodies specific for glutens, antibodies specific for tissue transglutaminase, the presence of pro-inflammatory T cells and cytokines, and degradation of the villus structure of the small intestine. Application of the methods and compositions of the invention can result in the improvement of any and all of these disease indicia of Celiac Sprue. Patients that can benefit from the present invention include both adults and children. Children in particular benefit from prophylactic treatment, as prevention of early exposure to toxic gluten peptides can prevent development of the disease into its more severe forms. Children suitable for prophylaxis in accordance with the methods of the invention can be identified by genetic testing for predisposition, e.g. by HLA typing; by family history, and by other methods known in the art. As is known in the art for other medications, and in accordance with the teachings herein, dosages of the tTGase inhibitors of the invention can be adjusted for pediatric use.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema.

Gluten proteins, which may include gliadins, secalins and hordeins, contain several sequences rich in Pro-Gln residues that are high-affinity substrates for TG2. TG2 is thought to be responsible for generating neoepitopes of gluten peptides through deamidation of glutamine residues. Presentation of these deamidated epitopes by DQ2 positive antigen presenting cells effectively stimulates proliferation of gliadin-specific T cells from intestinal biopsies of most Celiac Sprue patients. The toxic effects of gluten include immunogenicity of the gluten oligopeptides, leading to inflammation. TG2 also cross-links itself onto gliadin in vitro, and the cross-linked TGase might act as a hapten for the formation of antibodies against gluten peptides.

In addition to these conditions, it has been suggested that transglutaminase generates autoantibodies in a variety of autoimmune disorders by cross-linking potential autoantigens and acting as a hapten, e.g. in lupus, myasthenia gravis, multiple sclerosis, rheumatoid arthritis, etc. Anti-TG2 antibodies have been reported in lupus; and TG2 has been detected in the synovial fluid of arthritis patients, and the serum and cerebral spinal fluid of amyotrophic lateral sclerosis patients (see review by Kim et al. (2002) Neurochemistry International 40:85-103).

Inclusion body myositis is a progressive muscle disorder that affects older individuals. It is considered to be an autoimmune disease; associated with the expression of specific HLA molecules and a variety of autoantibodies. This disease is characterized by a progressively worsening weakness in the proximal and distal limbs that is resistant to steroid therapy. The histological features of this disease include distinctive rimmed vacuoles and filamentous inclusions, as well as mononuclear infiltrates, which consist predominantly of cytotoxic T cells. Total transglutaminase enzyme activity is elevated by 16-fold in diseased tissue, which is reflected in an increased number of $\epsilon$ ($\gamma$-glutamyl)lysine cross-links. This activity is apparently due to the increased expression of TG1 and TG2, which co-localize with deposits in vacuolated muscle fibers from patients with inclusion body myositis. The chronic inflammation that characterizes inclusion body myositis may also stimulate the expression of TG1 and TG2 and thereby contribute to the progressive nature of this disease.

In addition to autoimmune diseases, transglutaminases are associated with neurological conditions. Alzheimer's disease is associated with the selective loss of neurons in the neocortex, hippocampus, and amygdala, resulting in an impaired cognitive ability. This disease is also characterized by the presence of two types of protein aggregates: extracellular neuritic senile plaques, and intraneuronal neurofibrillary tangles. TGases are likely to contribute to the formation of these aggregates. Isoforms of TGase co-localize with the plaques and tangles in the brains of Alzheimer's disease patients and the number of $\epsilon$ ($\gamma$-glutamyl)lysine linkages in insoluble proteins from Alzheimer's disease brains is 30-50 times greater than the number found in normal brain tissues. In addition, total TGase activity is elevated in the affected areas of Alzheimer's disease brains, particularly TG1 and TG2. The components of plaques and tangles are substrates for TGases. For example, $\beta$ amyloid, which is found in a fibrillular form in plaques, is a substrate for TGases. Tau, the major component of the paired helical filaments that make up neurofibrillary tangles is also a substrate for TG2.

Huntington's disease is characterized by progressive motor and psychiatric disorders, as well as dementia. The most common manifestation of this disease is chorea: involuntary and non-directed motions that disrupt all normal activities eventually leading to death. The clinical progression of Huntington's disease is accompanied by specific neuronal loss and dysfunction, particularly in the striatum and later in the cerebral cortex. Huntington's disease is an autosomal dominant disease. The mutated gene and its product have been identified, and the protein found to be a substrate for TG2. Pathological mutations of the huntingtin gene, involving expansion of CAG repeats, result in stretches of polyglutamines of greater than 39 contiguous glutamine residues. The age of disease onset correlates inversely with the length of the polyglutamine expansion beyond the normal range, and there is a decrease in the age of disease onset with succeeding generations. There is elevated transglutaminase activity in the affected regions of diseased brains, including the striata. TG1, TG2 and TG3 are present in human brains, and all are elevated in Huntington's disease patient brains.

Parkinson's disease is characterized by tremor, bradykinesia, rigidity and postural instability. These motor disorders result primarily from a loss of dopaminergic neurons of the nigro-striatal pathway. Histologically, Parkinson's disease is characterized by a widespread distribution of Lewy bodies, which are intracytoplasmic aggregates of between 5 and 25 mm in diameter that feature a dense eosinophilic core and pale surrounding halo. Although Lewy bodies are thought to play a causative role in Parkinson's disease, these structures also have been identified in some cases of Alzheimer's disease. The major component of Lewy bodies is $\alpha$-synuclein. A fragment of $\alpha$-synuclein, known as the non-amyloid component (NAC), has been detected in the Lewy bodies of Parkinson's disease patients and the neuritic plaques of Alzheimer's disease patient. NAC is also as a substrate for transglutaminases, and is neurotoxic to primary dopaminergic neurons, as well as to neuroblastoma cells. TGases catalyze the formation of NAC polymers and aggregates of NAC and β-amyloid peptides.

Progressive supranuclear palsy is a motor disorder that initially presents in patients having unexpected falls. The later manifestations of the disease present as postural instability, vertical gaze palsy, axial rigidity, dysarthria and dementia. The most common pathological findings in this disease are midbrain atrophy with dilation of the aqueduct of Sylvius and depigmentation of the substantia nigra. These features are associated with the loss of neurons in the substantia nigra, globus pallidus, subthalamic nucleus, basal ganglia, diencephalon and brain stem. Neurofibrillary tangles occur in the affected areas of progressive supranuclear palsy patients. Tau, which is a substrate for transglutaminase, has also been identified as a major component of the detergent-insoluble proteins isolated from the brains of progressive supranuclear palsy patients. These aggregates also contain ε (γ-glutamyl) lysine cross links. Expression of TG1 and TG2, particularly TG1, are elevated in both the cerebellum of progressive supranuclear palsy patients.

Expression of transglutaminase has also been implicated in certain cancers, including glioblastoma, lung cancer, and cervical cancer. Hilton et al. (1997) *Neuropathol Appl Neurobiol.* 23(6):507-11 found expression of tissue transglutaminase in fibrillary astrocytomas, anaplastic astrocytomas and glioblastomas. Labeling was particularly prominent in the pseudopalisading tumour cells that surrounded foci of necrosis and apoptosis in glioblastomas. Strong transglutaminase labeling was also observed in the endothelial cells of vessels showing microvascular proliferation in all of the glioblastomas studied. Enhanced expression of transglutaminase by endothelial cells in glioblastomas may contribute to the high prevalence of vascular thrombosis and necrosis in these tumours. In cervical cancers, TG1 is overexpressed (see, for example, Friedrich et al. (1999) *Histochem J.* 31(1):13-8).

Cancer, as used herein, refers to hyperproliferative conditions. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Cancers include leukemias, lymphomas (Hodgkins and non-Hodgkins), sarcomas, melanomas, adenomas, carcinomas of solid tissue including breast cancer and pancreatic cancer, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like. Cancers that form solid tumors, i.e. other than leukemias and lymphomas, are of interest.

Cancer of particular interest are neurologic cancers, including brain tumors. Neurologic tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, primarily CNS glial tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are malignant, primitive tumors that arise in the posterior fossa, primarily in children. These tumors also occur in young adults. Medulloblastomas often are surgically resected with subsequent treatment with chemotherapy and/or radiation. They may recur locally or occasionally as drop metastasis from the posterior fossa to the spine. Meningiomas are common intracranial tumors that arise in the meninges and compress the underlying brain. Although typically considered benign and only rarely frankly malignant, management of these tumors often pose clinical challenges. Histological grades of meningiomas vary with the majority benign, WHO grade I/IV (82%); less commonly atypical, WHO II/IV (15%); and infrequently they occur as anaplastic or malignant, WHO grade III/IV (3%).

Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

The symptoms of both primary and metastatic brain tumors often depend on the location in the brain and the size of the tumor. Since various regions of the brain are responsible for specific functions, clinical symptoms will vary a great deal. Tumors in the frontal lobe of the brain may cause weakness and paralysis, mood disturbances, difficulty thinking, confusion and disorientation, and wide emotional mood swings. Parietal lobe tumors may cause seizures, numbness or paralysis, difficulty with handwriting, inability to perform simple mathematical problems, difficulty with certain movements, and loss of the sense of touch. Tumors in the occipital lobe can cause loss of vision in half of each visual field, visual hallucinations, and seizures. Temporal lobe tumors can cause seizures, perceptual and spatial disturbances, and receptive aphasia. If a tumor occurs in the cerebellum, the person may have ataxia, loss of coordination, headaches, and vomiting. Tumors in the hypothalamus may cause emotional changes, and changes in the perception of hot and cold. In addition, hypothalamic tumors may affect growth and nutrition in children. With the exception of the cerebellum, a tumor on one side of the brain causes symptoms and impairment on the opposite side of the body.

The compounds described herein are useful in the treatment of individuals suffering from the conditions described above, by administering an effective dose of a tTGase inhibitor, through a pharmaceutical formulation, and the like. Diagnosis of suitable patients may utilize a variety of criteria known to those of skill in the art.

Compounds of interest for inhibition of tTGase include those having the general formulae

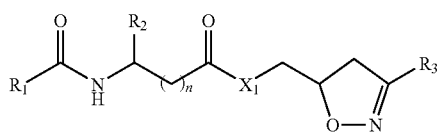

I

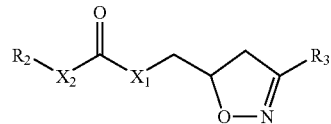

II where $R_1$, $R_2$ and $R_3$ are independently selected from H, alkyl, alkenyl, cycloalkyl, aryl, heteroalkyl, heteroaryl; alkoxy, alkylthio, arakyl, aralkenyl, halo, haloalkyl, haloalkoxy, heterocyclyl, and heterocyclylalkyl groups. $R_1$ and $R_2$ can also be an amino acid, a peptide, a peptidomimetic, or a peptidic protecting groups.

Illustrative $R_1$ groups include Cbz, Fmoc, and Boc. In other embodiments of the invention, $R_1$ is an arylether, aryl, alkylether or alkyl group, e.g. O-benzyl, benzyl, methyl or ethyl.

$R_2$ groups of interest include OMe, OtBu, Gly, and Gly-$NH_2$. In other embodiments, $R_2$ is selected from the group consisting of (s)-Bn, (s)-$CO_2Me$, (s)-Me, (R)-Bn, (S)—$CH_2CONHBn$, (S)-(1H-inol-yl)-methyl, and (S)-(4-hydrohy-phenyl)-methyl.

$R_3$ is preferably a halo group, i.e. F, Cl, Br, and I, more preferably Cl or Br.

$X_1$ and $X_2$ are selected from the group consisting of NH, O, and $NR_4$, where $R_4$ is a lower alkyl.

n is a whole number between 0 and 10, usually between 0 and 5, and more usually between 0 and 3.

The tTGase inhibitory compounds of the invention from the isoxazoles can be readily prepared using methods known in the art for other purposes and the teachings herein. Examples of synthetic routes to these compounds are also described in examples below For example, Castelhano et al have demonstrated that the dihydroisoxazole derivative (S)-1-[(3-Bromo-4,5-dihydro-isoxazol-5-ylmethyl)-carbamoyl]-2-phenyl-ethyl}-carbamic acid benzyl ester is an inhibitor of bovine epidermal transglutaminase (Castelhano et al., Bioorg. Chem. (1988) 16, 335-340; EP0237082).

A formula for transglutaminase inhibitors is:

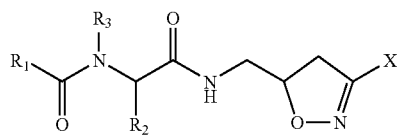

III where X is preferably a halo group, i.e. F, Cl, Br, and I.

$R_1$, $R_2$ and $R_3$ are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups, or may also be an amino acid, a peptide, a peptidomimetic, or a peptidic protecting groups.

Illustrative $R_1$ groups include Cbz, Fmoc, and Boc. In other embodiments of the invention, $R_1$ is an arylether, aryl, alkylether or alkyl group, e.g. O-benzyl, benzyl, methyl or ethyl.

$R_2$ groups of interest include OMe, OtBu, Gly, and Gly-$NH_2$. In other embodiments, $R_2$ is selected from the group consisting of (S)-Bn, (S)—$CO_2Me$, (s)-Me, (R)-Bn, (S)—$CH_2CONHBn$, (S)-(1H-inol-yl)-methyl, and (S)-(4-hydrohy-phenyl)-methyl.

$R_3$ groups of interest include H, and cyclic alkyl or aryl groups.

In some embodiments of the invention, the tTGase inhibitor is as set forth in formula III, where X is Br, $R_2$ is as defined above, and may include (S-),(R-)-4-fluoro-indole; (S-),(R-)-5-fluoro-indole; (S-),(R-)-6-fluoro-indole; (S-),(R-)-7-aza-indole; (S-)-p-hydroxyphenyl; (S-),(R-)-5-hydroxy-indole; (S-),(R-)-5-methoxy-indole; (S-)-5-fluoro-indole. $R_1$ is as defined above, and may specifically include O-benzyl or 3-yl-O-quinoline. Such compounds may have the structure:

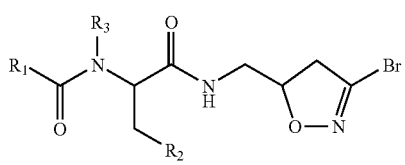

IV where $R_1$, $R_2$ and $R_3$ are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups, and can also be an amino acid, a peptide, a peptidomimetic, or a peptidic protecting groups.

Illustrative $R_1$ groups include arylether, cyclic alkylether, heteroarylether, particularly comprising N as a heteroatom.

$R_2$ groups of interest include substituted or unsubstituted heteroaryls, which include indoles substituted with one or more of Br, Cl, F, I, alkyl, particularly branched or unbranched lower alkyls of from one to 6 carbons, OH, aza, and methoxy groups.

$R_3$ groups of interest include H, or $R_2$ and $R_3$ may form a cyclic heteroalkyl or heteroaryl group.

Here we identify new compounds within this genus that are especially effective inhibitors of human tissue transglutaminase, and may therefore be used to treat conditions such as Celiac Sprue, cancer, dermatitis herpetiformis, etc.

tTGase inhibitors of interest also include analogs of the dioxoindoline isatin. The cyclic α-keto amide structure of isatin serves as a good analog of γ-carboxamide group of tTGase glutamyl substrate. α-keto amides are widely utilized as reversible inhibitors of cysteine-dependent proteases and, in a similar way, the hetetocyclic structure of isatin possesses an electrophilic carbonyl group which could be recognized by the enzyme as an analog of the substrate γ-carboxamide carbonyl group. Using standard procedures known in the art, the aromatic portion of the isatin structure can be derivatized further to incorporate additional functional groups into the inhibitors mimicking the other parts of peptide substrates.

The illustrative compounds of the invention described above were tested in a tTGase assay with recombinant human tissue transglutaminase, which was expressed, purified and assayed as described (Piper et al., *Biochemistry* (2001) 41, 386-393). Competitive inhibition with respect to the Cbz-Gln-Gly substrate was observed for all substrates; in all cases irreversible inactivation of the enzyme was also observed.

Methods are also shown for the synthesis of pure enantiomers of the above compounds. Using methods as set forth in the Examples, enantiopure dihydroisoxazole moieties are synthesized, and used to produce enantiopure compounds, which forms may find use in the methods of the invention. The tTGase inhibitors, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

To facilitate an appreciation of the invention, the tTGase inhibitors of the invention have in part been described above with structures containing variable "R" groups that are defined by reference to the various organic moieties that can be present at the indicated position in the structure. Below, brief definitions are provided for the phrases used to define the organic moieties listed for each R group.

As used herein, "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, 1,1-dimethylethyl(t-butyl), and the like. Unless stated otherwise specifically in the specification, the alkyl radical may be optionally substituted by hydroxy, alkoxy, aryloxy, haloalkoxy, cyano, nitro, mercapto, alkylthio, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkyl group that the substitution can occur on any carbon of the alkyl group.

"Alkoxy" refers to a radical of the formula —OR$_a$ where R$_a$ is an alkyl radical as defined above, e.g., methoxy, ethoxy, n-propoxy, 1-methylethoxy(iso-propoxy), n-butoxy, n-pentoxy, 1,1-dimethylethoxy(t-butoxy), and the like. Unless stated otherwise specifically in the specification, it is understood that for radicals, as defined below, that contain a substituted alkoxy group that the substitution can occur on any carbon of the alkoxy group. The alkyl radical in the alkoxy radical may be optionally substituted as described above.

"Alkylthio" refers to a radical of the formula —SR$_a$ where R$_a$ is an alkyl radical as defined above, e.g., methylthio, ethylthio, n-propylthio, 1-methylethylthio(isopropylthio), n-butylthio, n-pentylthio, 1,1-dimethylethylthio(t-butylthio), and the like. Unless stated otherwise specifically in the specification, it is understood that for radicals, as defined below, that contain a substituted alkylthio group that the substitution can occur on any carbon of the alkylthio group. The alkyl radical in the alkylthio radical may be optionally substituted as described above.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)—C(O)—$R^8$ where each $R^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkenyl group that the substitution can occur on any carbon of the alkenyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of hydroxy, alkoxy, aryloxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. The term "aryl" also refers to the compound $C_6H_5$, i.e. Bn.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aralkenyl" refers to a radical of the formula —$R_cR_b$ where $R_c$ is an alkenyl radical as defined above and $R_b$ is one or more aryl radicals as defined above, e.g., 3-phenylprop-1-enyl, and the like. The aryl radical(s) and the alkenyl radical may be optionally substituted as described above.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of aryl, halo, hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. The alkylene chain may be attached to the rest of the molecule through any two carbons within the chain.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of aryl, halo, hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. The alkenylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —O$R_c$, where $R_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzothiadiazolyl, benzoxazolyl, benzodioxolyl, benzodioxinyl, benzopyranyl, benzopyranonyl, benzofuranyl, benzofuranonyl, benzothienyl(benzothiophenyl), benzotriazolyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, halo, nitro, cyano, haloalkyl, haloalkoxy, aryl, heterocyclyl, heterocyclylalkyl, —O$R^8$, —$R^7$—O$R^8$, —C(O)O$R^8$, —$R^7$—C(O)O$R^8$, —C(O)N($R^8$)$_2$, —N($R^8$)$_2$, —$R^7$—N($R^8$)$_2$, and —N($R^8$)C(O)$R^8$ wherein each $R^7$ is a straight or branched alkylene or alkenylene chain and each $R^8$ is independently hydrogen, alkyl, alkenyl, cycloalkyl, cycloalkylalkyl, aralkyl or aryl.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above.

In the formulas provided herein, molecular variations are included, which may be based on isosteric replacement. "Isosteric replacement" refers to the concept of modifying chemicals through the replacement of single atoms or entire functional groups with alternatives that have similar size, shape and electro-magnetic properties, e.g. O is the isosteric replacement of S, N, COOH is the isosteric replacement of tetrazole, F is the isosteric replacement of H, sulfonate is the isosteric replacement of phosphate etc.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified through various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The present invention provides the tTGase inhibitors in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the tTGase inhibitors is achieved in various ways, although oral administration is a preferred route of administration. In some formulations, the tTGase inhibitors are systemic after administration; in others, the inhibitor is localized by virtue of the formulation, such as the use of an implant that acts to retain the active dose at the site of implantation.

In some pharmaceutical dosage forms, the tTGase inhibitors are administered in the form of their pharmaceutically acceptable salts. In some dosage forms, the tTGase inhibitor is used alone, while in others, the tTGase is used in combination with another pharmaceutically active compounds.

In combination therapies for the treatment of Celiac Sprue and/or Dermatitis Herpetiforms, the other active compound is, in some embodiments, a glutenase that can cleave or otherwise degrade a toxic gluten oligopeptide, as described in the Examples below.

In combination therapies for the treatment of cancer, the tTGase inhibitor may be combined with a cytotoxic agent, or administered in combination with radiation therapy. Cytotoxic agents that act to reduce cellular proliferation are known in the art and widely used. Such agents include alkylating agents, such as nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc.

Antimetabolite agents include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc.

Other natural products include azathioprine; brequinar; alkaloids and synthetic or semi-synthetic derivatives thereof, e.g. vincristine, vinblastine, vinorelbine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin;

anthraquinone glycosides, e.g. plicamycin (mithromycin); anthracenediones, e.g. mitoxantrone; aziridinopyrrolo indolediones, e.g. mitomycin; and the like.

Other chemotherapeutic agents include metal complexes, e.g. cisplatin (cis-DDP), carboplatin, etc.; ureas, e.g. hydroxyurea; and hydrazines, e.g. N-methylhydrazine. Other antiproliferative agents of interest include immunosuppressants, e.g. mycophenolic acid, thalidomide, desoxyspergualin, azasporine, leflunomide, mizoribine, azaspirane (SKF 105685), etc.

The antineoplastic agents taxols (or taxanes) hyperstabilize polymerized microtubules, leading to mitotic arrest and cytotoxicity in proliferating cells. Taxanes (or taxols), such as paclitaxel, docetaxel, etc. are of interest. Also of interest are the microtubule stabilizing epothilones (see Bollag et al. (1995) Cancer Research, Vol 55, Issue 11 2325-2333, herein incorporated by reference with respect to teachings of the class, and use thereof of these chemotherapeutic agents), e.g. epothilone A and epothilone B.

Retinoids, e.g. vitamin A, 13-cis-retinoic acid, trans-retinoic acid, isotretinoin, etc.; carotenoids, e.g. beta-carotene, vitamin D, etc. Retinoids regulate epithelial cell differentiation and proliferation, and are used in both treatment and prophylaxis of epithelial hyperproliferative disorders.

Topoisomerase inhibitors of interest include irinotecan (CPT-11), a topoisomerase I inhibitor. Other topoisomerase inhibitors of interest in the subject methods include doxorubicin and carboplatinum, which inhibit type II topoisomerase.

In the such embodiments for the treatment of cancer, a cytotoxic agent may be an alkylating agent such as BCNU or temozolomide, an antimitotic agent such as a taxane or epothilone, or arginine deiminase.

Pharmaceutical Formulations: The tTGase inhibitors can be incorporated into a variety of formulations for therapeutic administration. In combination therapies, the tTGase inhibitor and second agent can be delivered simultaneously, or within a short period of time, by the same or by different routes. In one embodiment of the invention, a co-formulation is used, where the two components are combined in a single suspension. Alternatively, the two may be separately formulated.

Part of the total dose may be administered by different routes. Such administration may use any route that results in systemic absorption, by any one of several known routes, including but not limited to inhalation, i.e. pulmonary aerosol administration; intranasal; sublingually; orally; and by injection, e.g. subcutaneously, intramuscularly, etc.

For injectables, the agents are used in formulations containing cyclodextrin, cremophor, DMSO, ethanol, propylene glycol, solutol, Tween, triglyceride and/or PEG. For oral preparations, the agents are used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and in some embodiments, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations of the tTGase inhibitors of the invention comprise engineered polymer microspheres made of biologically erodable polymers, which display strong adhesive interactions with gastrointestinal mucus and cellular linings, can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18.

In another embodiment, the tTGase inhibitor or formulation thereof is admixed with food, or used to pre-treat foodstuffs containing glutens.

Formulations are typically provided in a unit dosage form, where the term "unit dosage form," refers to physically discrete units suitable as unitary dosages for human subjects, each unit containing a predetermined quantity of tTGase inhibitor calculated in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Depending on the patient and condition being treated and on the administration route, the tTGase inhibitor is administered in dosages of 1 mg to 2000 mg/kg body weight per day, e.g. about 100, 500, 1000, 10,000 mg/day for an average person. Durations of the regimen may be from: 1×, 2×3× daily; and in a combination regimen may be from about 1, about 7, about 14, etc. days prior to administration of second agent. Dosages are appropriately adjusted for pediatric formulation. Those of skill will readily appreciate that dose levels can vary as a function of the specific inhibitor, the diet of the patient and the gluten content of the diet, the severity of the symptoms, and the susceptibility of the subject to side effects. Some of the inhibitors of the invention are more potent than others. Preferred dosages for a given inhibitor are readily determinable by those of skill in the art by a variety of means. A preferred means is to measure the physiological potency of a given compound.

Various methods for administration are employed in the practice of the invention. In one preferred embodiment, oral administration, for example with meals, is employed. The dosage of the therapeutic formulation can vary widely, depending upon the nature of the disease, the frequency of administration, the manner of administration, the clearance of the agent from the patient, and the like. The initial dose can be larger, followed by smaller maintenance doses. The dose can be administered as infrequently as weekly or biweekly, or more often fractionated into smaller doses and administered daily, with meals, semi-weekly, and the like, to maintain an effective dosage level.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Synthesis of Dihydroxyisoxazole Containing tTGase Inhibitors

Synthesis of {(S)-1-[(3-Bromo-4,5-dihydro-isoxazol-5-ylmethyl)-carbamoyl]-2-phenyl-ethyl}-carbamic acid benzyl ester (n=0, X=NH, $R_1$=BnO, $R_2$=(S)-Bn, $R_3$=Br) (49). N-Cbz-L-Phe (0.30 g, 1.0 mmol) and HOBt (0.15 g, 1.1 eq) were dissolved in 2 mL DMF. 3-Bromo-5-aminomethyl-4,5-dihydroisoazole (0.18 g, 1.0 eq), prepared following a reported procedure (Rohloff et al. (1992) *Tetrahedron Lett.* 33(22):3113-3116), was added to the solution cooled in an ice bath followed by EDCI (0.23 g, 1.2 eq). The ice bath was removed and the stirring was continued overnight. The solution was diluted with ethyl acetate and washed with sat. $NaHCO_3$ solution and brine. The organic layer was dried over $MgSO_4$ and filtered. The solvent was removed by evaporation and the residue was purified by $SiO_2$ chromatography to give the title compound as a white solid (0.24 g, 52%).

$^1$H NMR (CDCl$_3$, 200 MHz): δ=7.34-7.26 (m, 8H), 7.17 (d, 2H, J=7.6 Hz), 6.19-6.09 (m, 1H), 5.21-5.15 (m, 1H), 5.09 (s, 2H), 4.74-4.60 (m, 1H), 4.41-4.36 (m, 1H), 3.49-3.45 (m, 2H), 3.26-3.12 (m, 1H), 3.07 (d, 2H, J=6.8 Hz), 2.97-2.76 (m, 1H) MS (ESI): m/z=460.1 [M+H]$^+$, 482.2 [M+Na]$^+$

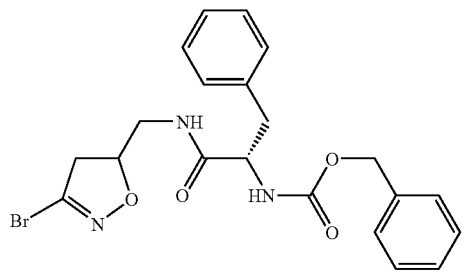

49

{(S)-1-[(3-Bromo-4,5-dihydro-isoxazol-5-ylmethyl)-carbamoyl]-2-phenyl-ethyl}-carbamic acid benzyl ester Synthesis of (S)-2-Benzyloxycarbonylamino-4-[(3-bromo-4,5-dihydro-isoxazol-5-ylmethyl)-carbamoyl]-butyric acid methyl ester (n=2, X=NH, $R_1$=BnO, $R_2$=(S)—$CO_2$Me, $R_3$=Br) (50). The title compound was prepared according to the procedure for compound 49 except using N-Cbz-L-Glu-OMe.

$^1$H NMR (CDCl$_3$, 200 MHz): δ=7.41-7.30 (m, 5H), 6.22-6.12 (m, 1H), 5.63-5.57 (m, 1H), 5.11 (s, 2H), 4.82-4.74 (m, 1H), 4.41-4.33 (m, 1H), 3.75 (s, 3H), 3.54-3.48 (m, 2H), 3.32-3.15 (m, 1H), 3.02-2.88 (m, 1H), 2.34-2.22 (m, 3H), 2.05-1.94 (m, 1H) MS (ESI): m/z=456.1 [M+H]$^+$, 478.2 [M+Na]$^+$

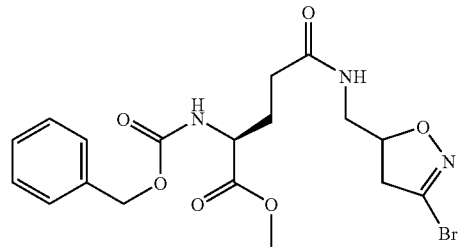

50

(S)-2-Benzyloxycarbonylamino-4-[(3-bromo-4,5-dihydro-isoxazol-5-ylmethyl)-carbamoyl]-butyric acid methyl ester Synthesis of (S)-2-Benzyloxycarbonylamino-N-(3-bromo-4,5-dihydro-isoxazol-5-ylmethyl)-succinamic acid methyl ester (n=1, X=NH, $R_1$=BnO, $R_2$=(S)—$CO_2$Me, $R_3$=Br) (51). The title compound was prepared according to the procedure for compound 49 except using N-Cbz-L-Asp-OMe.

$^1$H NMR (CDCl$_3$, 200 MHz): δ=7.37-7.30 (m, 5H), 6.00-5.90 (m, 2H), 5.13 (s, 2H), 4.80-4.71 (m, 1H), 4.63-4.58 (m, 1H), 3.76 (s, 3H), 3.54-3.44 (m, 2H), 3.33-3.23 (m, 1H), 2.99-2.70 (m, 3H) MS (ESI): m/z=442.1 [M+H]$^+$, 464.2 [M+Na]$^+$

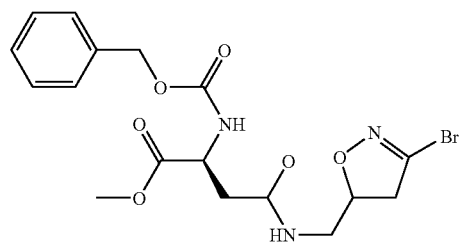

51

(S)-2-Benzyloxycarbonylamino-N-(3-bromo-4,5-dihydro-isoxazol-5-ylmethyl)-succinamic acid methyl ester Synthesis of (S)-2-Benzyloxycarbonylamino-3-phenyl-propionic acid 3-bromo-4,5-dihydro-isoxazol-5-ylmethyl ester (n=0, X=O, $R_1$=BnO, $R_2$=(S)-Bn, $R_3$=Br) (52). N-Cbz-L-Phe (0.30 g, 1.0 mmol) was dissolved in the mixture of acetonitrile (6 mL), DIEA (0.18 mL, 1.0 eq) and excess allyl bromide (3 mL). After the reaction was allowed to proceed overnight, the reaction mixture was diluted with ethyl acetate, washed with sat. $Na_2CO_3$ solution and brine, dried over $MgSO_4$ and concentrated to provide the ally ester as a clear oil (0.34 g, quant.). The ester (0.19 g, 0.57 mmol) and dibromoformaldoxime (0.14 g, 1.1 eq) were dissolved in 3 mL ethyl acetated and $NaHCO_3$ (0.21 g, 4.3 eq) was added to the solution. The reaction mixture was stirred overnight, diluted with ethyl acetated and washed with sat. $NaHCO_3$ solution and brine. The organic layer was dried over $MgSO_4$ and the solvent was removed by evaporation. The residue was purified by $SiO_2$ chromatography to give the title compound as a white solid (0.159, 58%)

$^1$H NMR (CDCl$_3$, 200 MHz): δ=7.35-7.26 (m, 8H), 7.16-7.14 (m, 2H), 5.20-5.05 (m, 3H), 4.85-4.79 (m, 1H), 4.68-4.63 (m, 1H), 4.22-4.15 (m, 2H), 3.27-3.09 (m, 3H), 2.96-2.77 (m, 1H) MS (ESI): m/z=461.1 [M+H]$^+$, 483.2 [M+Na]$^+$

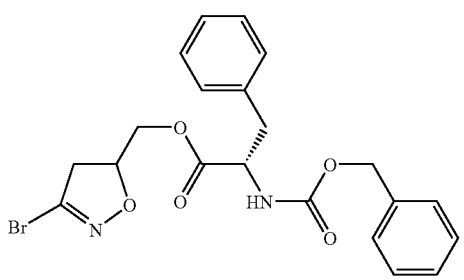

(S)-2-Benzloxycarbonylamino-3-phenyl-propionic acid 3-bromo-4,5-dihydro-isoxazol-5-ylmethyl ester Synthesis of {(S)-1-[(3-Bromo-4,5-dihydro-isoxazol-5-ylmethyl)-carbamoyl]-ethyl}-carbamic acid benzyl ester (n=0, X=NH, $R_1$=BnO, $R_2$=(S)-Me, $R_3$=Br) (53). The title compound was prepared according to the procedure for compound 49 except using N-Cbz-L-Ala.

$^1$H NMR (CDCl$_3$, 200 MHz): δ=7.37-7.34 (b, 5H), 6.68-6.45 (m, 1H), 5.24-5.18 (m, 1H), 5.13 (s, 2H), 4.80-4.76 (m, 1H), 4.26-4.18 (m, 1H), 3.55-3.47 (m, 2H), 3.33-3.19 (m, 1H), 3.05-2.92 (m, 1H), 1.39 (d, 3H, J=7.0 Hz) MS (ESI): m/z=384.1 [M+H]$^+$, 406.1 [M+Na]$^+$

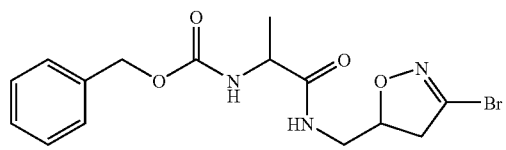

{(S)-1-[(3-Bromo-4,5-dihydro-isoxazol-5-ylmethyl)-carbamoyl]-ethyl}-carbamic acid benzyl ester Synthesis of (S)-2-Acetylamino-N-(3-bromo-4,5-dihydro-isoxazol-5-ylmethyl)-3-phenyl-propionamide (n=0, X=NH, $R_1$=Me, $R_2$=(S)-Bn, $R_3$=Br) (54). The title compound was prepared according to the procedure for compound 49 except using N-Ac-L-Phe.

$^1$H NMR (CDCl$_3$, 200 MHz): δ=7.33-7.18 (m, 5H), 6.14-6.09 (m, 1H), 6.02-5.97 (m, 1H), 4.67-4.59 (m, 2H), 3.49-3.41 (m, 2H), 3.22-3.03 (m, 3H), 2.97-2.70 (m, 1H), 2.00 (s, 3H) MS (ESI): m/z=368.1 [M+H]$^+$, 390.2 [M+Na]$^+$

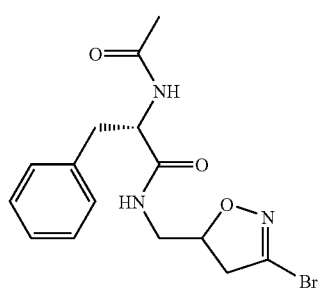

(S)-2-Acetylamino-N-(3-bromo-4,5-dihydro-isoxazol-5-ylmethyl)-3-phenyl-propionamide Synthesis of {(R)-1-[(3-Bromo-4,5-dihydro-isoxazol-5-ylmethyl)-carbamoyl]-2-phenyl-ethyl}-carbamic acid benzyl ester (n=0, X=NH, $R_1$=BnO, $R_2$=(R)-Bn, $R_3$=Br) (55). The title compound was prepared according to the procedure for compound 49 except using N-Cbz-D-Phe.

$^1$H NMR (CDCl$_3$, 200 MHz): δ=7.34-7.26 (m, 8H), 7.17 (d, 2H, J=7.8 Hz), 6.19-6.09 (m, 1H), 5.21-5.15 (m, 1H), 5.09 (s, 2H), 4.74-4.60 (m, 1H), 4.41-4.36 (m, 1H), 3.49-3.45 (m, 2H), 3.26-3.12 (m, 1H), 3.07 (d, 2H, J=7.0 Hz), 2.97-2.76 (m, 1H) MS (ESI): m/z=460.1 [M+H]$^+$, 482.2 [M+Na]$^+$

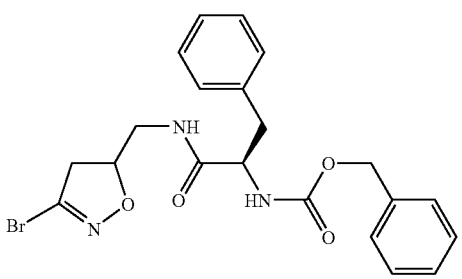

{(R)-1-[(3-Bromo-4,5-dihydro-isoxazol-5-ylmethyl)-carbamoyl]-2-phenyl-ethyl}-carbamic acid benzyl ester Synthesis of {(S)-2-Benzylcarbamoyl-1-[(3-bromo-4,5-dihydro-isoxazol-5-ylmethyl)-carbamoyl]-ethyl}-carbamic acid benzyl ester (n=0, X=NH, $R_1$=BnO, $R_2$=(S)—CH$_2$CONHBn, $R_3$=Br) (56). The title compound was prepared according to the procedure for compound 49 except using β-bezylamide of N-Cbz-L-Asp ((S)—N-Benzyl-2-benzyloxycarbonylamino-succinamic acid).

$^1$H NMR (CDCl$_3$, 400 MHz): δ=7.38-7.24 (m, 1H), 6.43-6.40 (m, 1H), 6.01-5.99 (m, 1H), 5.14 (s, 2H), 4.80-4.70 (m, 1H), 4.58-4.52 (m, 1H), 4.41 (d, 2H, J=6.4 Hz), 3.57-3.50 (m, 2H), 3.25-3.12 (m, 1H), 3.00-3.94 (m, 2H), 2.62-2.56 (m, 1H) MS (ESI): m/z=517.1 [M+H]$^+$, 539.2 [M+Na]$^+$

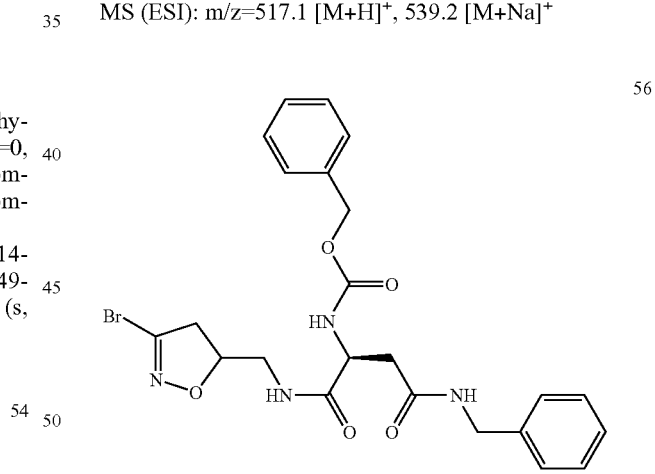

{(S)-2-Benzylcarbamoyl-1-[(3-bromo-4,5dihydro-isoxazol-5-ylmethyl)-carbamoyl]-ethyl}-carbamic acid Synthesis of [(S)-1-[(3-Bromo-4,5-dihydro-isoxazol-5-ylmethyl)-carbamoyl]-2-(1H-indol-3-yl)-ethyl]-carbamic acid benzyl ester (n=0, X=NH, $R_1$=BnO, $R_2$=(S)-(1H-indol-3-yl)-methyl, $R_3$=Br) (57). The title compound was prepared according to the procedure for compound 49 except using N-Cbz-L-Trp.

$^1$H NMR (CDCl$_3$, 400 MHz): δ=8.14 (br, 1H), 7.70-7.63 (m, 1H), 7.37-7.31 (m, 6H), 7.22-7.18 (m, 1H), 7.13-7.09 (m, 1H), 7.04-7.02 (m, 1H), 6.15-6.10 (m, 1H), 5.45-5.39 (m, 1H), 5.14-5.06 (m, 2H), 4.59-4.47 (m, 2H), 3.40-3.31 (m, 3H), 3.20-3.14 (m, 1H), 3.11-3.04 (m, 1H), 2.82-2.74 (m, 1H) MS (ESI): m/z=499.0 [M+H]$^+$, 521.2 [M+Na]$^+$

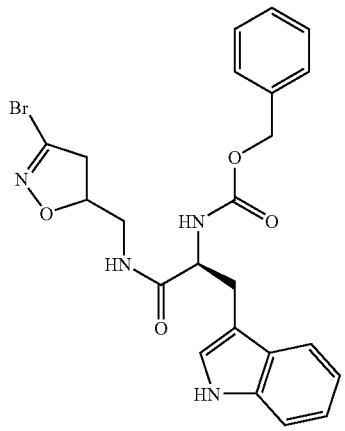

[(S)-1-[(3-Bromo-4,5-dihydro-isoxazol-5-ylmethyl)-carbamoyl]-2-(1H-indol-3-yl)-ethyl]-carbamic acid benzyl ester Synthesis of {(S)-1-[(3-Bromo-4,5-dihydro-isoxazol-5-ylmethyl)-methyl-carbamoyl]-2-phenyl-ethyl}-carbamic acid benzyl ester (n=0, X=NMe, $R_1$=BnO, $R_2$=(S)-Bn, $R_3$=Br) (58). The title compound was prepared according to the procedure for compound 52 except using N-methylallylamine.

$^1$H NMR (CDCl$_3$, 400 MHz): δ=7.34-7.26 (m, 8H), 7.18-7.16 (m, 2H), 5.57-5.56 (m, 1H), 5.12-5.05 (m, 2H), 4.93-4.73 (m, 2H), 3.80-3.67 (m, 1H), 3.36-3.17 (m, 2H), 3.02-3.86 (m, 6H)

MS (ESI): m/z=474.2 [M+H]$^+$, 496.3 [M+Na]$^+$

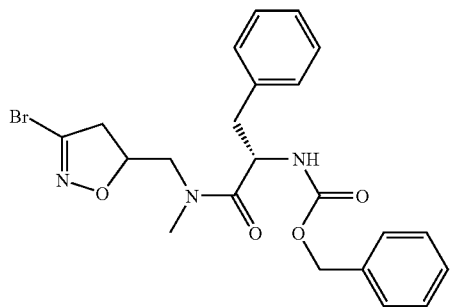

[(S)-1-[(3-Bromo-4,5-dihydro-isoxazol-5-ylmethyl)-methyl-carbamoyl]-2-(4-hydroxy-phenyl)-ethyl]-carbamic acid benzyl ester Synthesis of [(S)-1-[(3-Bromo-4,5-dihydro-isoxazol-5-ylmethyl)-methyl-carbamoyl]-2-(4-hydroxy-phenyl)-ethyl]-carbamic acid benzyl ester (n=0, X=NH, $R_1$=BnO, $R_2$=(S)-(4-hydroxy-phenyl)-methyl, $R_3$=Br) (59). The title compound was prepared according to the procedure for compound 49 except using N-Cbz-L-Tyr.

$^1$H NMR (DMSO-d$_6$, 400 MHz): δ=9.17 (br, 1H), 8.27-8.23 (m, 1H), 7.43-7.40 (m, 1H), 7.32-7.22 (m, 5H), 7.03 (d, 2H, J=7.6 Hz), 6.62 (d, 2H, J=7.6 Hz), 4.93 (s, 2H), 4.68-4.64 (m, 1H), 4.13-4.11 (m, 1H), 3.37-3.19 (m, 3H), 3.05-2.90 (m, 1H), 2.81-2.77 (m, 1H), 2.63-2.58 (m, 1H)

MS (ESI): m/z=476.1 [M+H]$^+$, 498.2 [M+Na]$^+$

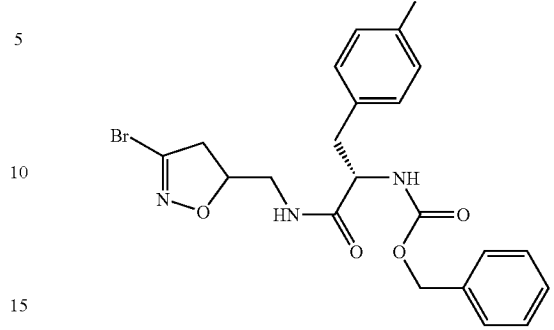

[(S)-1-[(3-Bromo-4,5-dihydro-isoxazol-5-ylmethyl)-methyl-carbamoyl]-2-(4-hydroxy-phenyl)-ethyl]-carbamic acid benzyl ester Synthesis of 1-(3-Bromo-4,5-dihydro-isoxazol-5-ylmethyl)-3-phenyl-urea ($X_1$=NH, $X_2$=NH, $R_2$=Ph, $R_3$=Br) (60). 3-Bromo-5-aminomethyl-4,5-dihydroisoazole (20 mg, 0.11 mmol) and phenyl isocyanate (13 uL, 1.0 eq) were dissolved in the mixture of THF (0.5 mL) and DMF (0.1 mL). After 30 min of stirring, the mixture was diluted with ethyl acetate and washed with brine. The organic layer was dried over Na$_2$SO$_4$ and the solvents were removed by evaporation. The residue was purified by SiO$_2$ chromatography to give the title compound.

$^1$H NMR (acetone-d$_6$, 400 MHz): δ=8.02 (br, 1H), 7.50 (d, 2H), 7.25-7.20 (m, 2H), 6.93 (t, 1H), 6.24 (br, 1H), 4.90-4.86 (m, 1H), 3.56-3.54 (m, 2H), 3.48-3.41 (m, 1H), 3.19-3.13 (m, 1H)

MS (ESI): m/z=298.0 [M+H]$^+$

Synthesis of 1-(3-Bromo-4,5-dihydro-isoxazol-5-ylmethyl)-3-(2-chloro-5-trifluoromethyl-phenyl)-urea ($X_1$=NH, $X_2$=NH, $R_2$=2-chloro-5-trifluoromethyl-phenyl, $R_3$=Br) (61). The title compound was prepared according to the procedure for compound 60 except using 2-chloro-5-trifluoromethyl-phenylisocyanate $^1$H NMR (acetone-d$_6$, 400 MHz): δ=8.82 (s, 1H), 8.12 (br, 1H), 7.62 (d, 1H, J=8.0 Hz), 7.30 (d, 1H, J=8.0 Hz), 6.90 (br, 1H), 4.93-4.87 (m, 1H), 3.57-3.54 (m, 2H), 3.49-3.42 (m, 1H), 3.20-3.14 (m, 1H)

MS (ESI): m/z=400.0 [M+H]$^+$

Synthesis of 1-(3-Bromo-4,5-dihydro-isoxazol-5-ylmethyl)-3-(4-chloro-2-trifluoromethyl-phenyl)-urea ($X_1$=NH, $X_2$=NH, $R_2$=4-chloro-2-trifluoromethyl-phenyl, $R_3$=Br) (62). The title compound was prepared according to the procedure for compound 60 except using 4-chloro-2-trifluoromethyl-phenylisocyanate.

$^1$H NMR (acetone-d$_6$, 400 MHz): δ=8.20 (d, 1H, J=7.6 Hz), 7.66 (br, 1H), 7.62-7.60 (m, 2H), 6.82 (br, 1H), 4.89-4.85 (m, 1H), 3.55-3.51 (m, 2H), 3.47-3.40 (m, 1H), 3.18-3.12 (m, 1H)

MS (ESI): m/z=400.0 [M+H]$^+$

Synthesis of 1-(3-Bromo-4,5-dihydro-isoxazol-5-ylmethyl)-3-(4-fluoro-phenyl)-urea ($X_1$=NH, $X_2$=NH, $R_2$=4-fluoro-phenyl, $R_3$=Br) (63). The title compound was prepared according to the procedure for compound 60 except using 4-fluoro-phenylisocyanate.

$^1$H NMR (acetone-d$_6$, 200 MHz): δ=8.06 (br, 1H), 7.47-7.40 (m, 2H), 6.99-6.90 (m, 2H), 5.94 (br, 1H), 4.82-4.76 (m, 1H), 3.45-3.30 (m, 3H), 3.17-3.04 (m, 1H)

MS (ESI): m/z=316.0 [M+H]$^+$

Synthesis of 1-(3-Bromo-4,5-dihydro-isoxazol-5-ylmethyl)-3-(2,5-dimethyl-phenyl)-urea ($X_1$=NH, $X_2$=NH, $R_2$=2,5-dimethyl-phenyl, $R_3$=Br) (64). The title compound was prepared according to the procedure for compound 60 except using 2,5-dimethyl-phenylisocyanate.

MS (ESI): m/z=326.0 $[M+H]^+$

Example 2

Synthesis of Dioxoindole Containing tTGase Inhibitors

Synthesis of 2,3-Dioxo-2,3-dihydro-1H-indole-5-sulfonic acid propylamide. 2,3-Dioxo-2,3-dihydro-1H-indole-5-sulfonyl chloride (0.10 g, 0.41 mmol), prepared by the reaction of the sodium salt of 5-isatinsulfonic acid with $POCl_3$, was dissolved in 5 mL THF. This solution was cooled in an ice bath and DIEA (0.14 mL, 2.0 eq) was added slowly, followed by n-propylamine (35 uL, 1.0 eq). Stirring was continued for 40 min and the solution was diluted with ethyl acetate and washed with brine. The organic layer was dried over $Na_2SO_4$ and the solvent was removed by evaporation. The residue was purified by $SiO_2$ chromatography to give the title compound (65 mg, 60%).

$^1$H NMR ($CD_3CN$, 400 MHz): δ=9.17 (br, 1H), 8.02 (d, 1H, J=8.0 Hz), 7.93 (s, 1H), 7.13 (d, 1H, J=8.0 Hz), 5.62-5.58 (m, 1H), 2.85-2.80 (m, 2H), 1.48-1.42 (m, 2H), 0.85 (t, 3H, J=7.2 Hz)

MS (ESI): m/z=−267.1 $[M-H]^-$

Synthesis of 2,3-Dioxo-2,3-dihydro-1H-indole-5-sulfonic acid benzylamide. The title compound was prepared from benzyl amine following the procedure for 2,3-Dioxo-2,3-dihydro-1H-indole-5-sulfonic acid propylamide.

$^1$H NMR ($CD_3CN$, 400 MHz): δ=9.19 (br, 1H), 7.98 (d, 1H, J=8.4 Hz), 7.85 (s, 1H), 7.31-7.21 (m, 5H), 7.07 (d, 1H, J=8.4 Hz), 6.11 (t, 1H, J=6.3 Hz), 4.11 (d, 2H, J=6.3 Hz)

MS (ESI): m/z=−315.2 $[M-H]^-$

Synthesis of (S)-1-(2,3-Dioxo-2,3-dihydro-1H-indole-5-sulfonyl)-pyrrolidine-2-carboxylic acid methyl ester. The title compound was prepared from L-Pro-OMe following the procedure for 2,3-Dioxo-2,3-dihydro-1H-indole-5-sulfonic acid propylamide.

$^1$H NMR ($CDCl_3$, 200 MHz): δ=8.85 (br, 1H), 8.15-8.11 (m, 2H), 7.11 (d, 1H, J=8.8 Hz), 4.47-4.41 (m, 1H), 3.74 (s, 3H), 3.45-3.39 (m, 2H), 2.20-1.94 (m, 4H)

MS (ESI): m/z=338.9 $[M+H]^+$

Synthesis of (S)-2-(2,3-Dioxo-2,3-dihydro-1H-indole-5-sulfonylamino)-3-phenyl-propionamide. The title compound was prepared from L-Phe-$NH_2$ following the procedure for 2,3-Dioxo-2,3-dihydro-1H-indole-5-sulfonic acid propylamide.

$^1$H NMR ($CD_3CN$, 200 MHz): δ=10.70 (br, 1H), 7.78 (d, 1H, J=8.4 Hz), 7.64 (s, 1H), 7.15-7.06 (m, 6H), 6.90 (d, 1H, J=8.4 Hz), 6.79 (br, 1H), 6.08 (br, 1H), 3.98-3.87 (m, 1H), 3.04-2.95 (m, 1H), 2.76-2.64 (m, 1H)

MS (ESI): m/z=−372.2 $[M-H]^-$

Synthesis of (S)—N-(2-Dimethylamino-ethyl)-2-(2,3-dioxo-2,3-dihydro-1H-indole-5-sulfonyl amino)-3-phenyl-propionamide. The title compound was prepared from L-Phe-$NHCH_2CH_2NMe_2$ following the procedure for 2,3-Dioxo-2,3-dihydro-1H-indole-5-sulfonic acid propylamide.

$^1$H NMR ($CD_3CN$, 400 MHz): δ=7.84 (d, 1H, J=8.0 Hz), 7.69 (s, 1H), 7.22-7.12 (m, 6H), 6.98 (d, 1H, J=8.0 Hz), 6.76 (br, 1H), 3.96-3.93 (m, 1H), 3.10-3.02 (m, 2H), 3.00-2.95 (m, 1H), 2.78-2.72 (m, 1H), 2.22-2.17 (m, 2H), 2.15 (s, 6H)

MS (ESI): m/z=445.2 $[M+H]^+$

Synthesis of 6-Bromo-7-methyl-1H-indole-2,3-dione. Chloral alcoholate (0.43 g, 1.05 eq) and $Na_2SO_4$ (2.84 g, 20 mmol) were dissolved in 10 mL water. 3-Bromo-2-methylaniline (0.33 g, 1.77 mmol) was added to the solution followed by 0.16 mL conc. HCl aqueous solution and $NH_2OH\cdot HCl$ (0.38 g, 3.0 eq). The mixture was refluxed for 15 min and stirring was continued for additional 1 hr at RT. The precipitate was collected by filtration, washed with water and dried under vacuum. This precipitate was dissolved in 1 mL $H_2SO_4$ and the solution was heated (80° C.) for 15 min. After cooling down to RT, the mixture was poured into ice-water mixture and the precipitate was collected, washed with water and dried under vacuum to give the title compound (0.26 g, 61%).

$^1$H NMR ($CD_3CN$, 200 MHz): δ=9.02 (BR, 1 h), 7.38 (d, 1H, J=7.8 Hz), 7.30 (d, 1H, J=7.8 Hz), 2.30 (s, 3H)

MS (ESI): m/z=−238.2 $[M-H]^-$

Synthesis of 7-Methyl-6-phenyl-1H-indole-2,3-dione. 6-Bromo-7-methyl-1H-indole-2,3-dione (100 mg, 0.38 mmol) and phenylboronic acid (53 mg, 1.1 eq) were dissolved in 10 mL DME. $Pd(PPh_3)_4$ (22 mg, 0.05 eq) were added followed by $NaHCO_3$ (65 mg, 2.0 eq) dissolved in 10 mL water. The mixture was refluxed for 2.5 hr and the organic solvent was removed by evaporation. The mixture was extracted with ethyl acetate and the combined organic layers were dried over $Na_2SO_4$ and purified by $SiO_2$ chromatography to give the title compound (50 mg, 51%).

$^1$H NMR ($CDCl_3$, 400 MHz): δ=8.53 (br, 1H), 7.52 (d, 1H, J=7.6 Hz), 7.49-7.43 (m, 3H), 7.31 (d, 2H, J=6.4 Hz), 7.03 (d, 1H, J=7.6 Hz), 2.16 (s, 3H)

MS (ESI): m/z=−236.3 $[M-H]^-$

Inhibition of tTG. tTG (9 μM) was inactivated in 200 mM MOPS, pH=7.1, 5 mM $CaCl_2$, 1 mM ETDA at 30° C. containing 0-600 μM Pro-Gln-Pro-Aci-Leu-Pro-Tyr. Every 20 minutes a 40 μl aliquot was removed and residual tTG activity was assayed in 0.5 ml reaction containing 200 mM MOPS, pH=7.1, 5 mM $CaCl_2$, 1 mM ETDA, 10 mM α-ketoglutarate, 180 U/ml glutamate dehydrogenase (Biozyme laboratories) at 30° C. for 20 minutes by measuring the decrease of absorption at 340 nm. Residual activity was corrected by the corresponding uninhibited tTG reaction (0 μM inhibitor) and fitted to an exponential decay. Kinetic parameters were obtained by double-reciprocal plotting of the apparent second-order inactivation constant or, for isatin analogs, by fitting the data for reversible inhibitors to a standard Michaelis Menten equation with a competitive inhibition constant. The results of these inhibition experiments are shown in Tables 1 and 2 below.

TABLE 1

Tissue transglutaminase inhibition by dihydroisoxazoles

| Tested Compound | $K_i$ (M) | $k_{inh}$ (min$^{-1}$) | $k_{inh}/K_i$ (min$^{-1}$M$^{-1}$) |
|---|---|---|---|
| {(S)-1-[(3-Bromo-4,5-dihydro-isoxazol-5-ylmethyl)-carbamoyl]-2-phenyl-ethyl}-carbamic acid benzyl ester (49) | $0.73 \times 10^{-3}$ | 1.4 | 1900 |
| (S)-2-Benzyloxycarbonylamino-4-[(3-bromo-4,5-dihydro-isoxazol-5-ylmethyl)-carbamoyl]-butyric acid methyl ester (50) | $1.6 \times 10^{-3}$ | 0.32 | 200 |

TABLE 1-continued

Tissue transglutaminase inhibition by dihydroisoxazoles

| Tested Compound | $K_i$ (M) | $k_{inh}$ (min$^{-1}$) | $k_{inh}/K_i$ (min$^{-1}$M$^{-1}$) |
|---|---|---|---|
| ) (S)-2-Benzyloxycarbonylamino-N-(3-bromo-4,5-dihydro-isoxazol-5-ylmethyl)-succinamic acid methyl ester (51) | $0.87 \times 10^{-3}$ | 0.43 | 490 |
| (S)-2-Benzyloxycarbonylamino-3-phenyl-propionic acid 3-bromo-4,5-dihydro-isoxazol-5-ylmethyl ester (52) | $1.3 \times 10^{-3}$ | 0.32 | 230 |
| {(S)-1-[(3-Bromo-4,5-dihydro-isoxazol-5-ylmethyl)-carbamoyl]-ethyl}-carbamic acid benzyl ester (53) | $0.91 \times 10^{-3}$ | 0.41 | 450 |
| (S)-2-Acetylamino-N-(3-bromo-4,5-dihydro-isoxazol-5-ylmethyl)-3-phenyl-propionamide (54) | $2.7 \times 10^{-3}$ | 0.60 | 220 |
| {(R)-1-[(3-Bromo-4,5-dihydro-isoxazol-5-ylmethyl)-carbamoyl]-2-phenyl-ethyl}-carbamic acid benzyl ester (55) | $0.31 \times 10^{-3}$ | 0.29 | 940 |
| {(S)-2-Benzylcarbamoyl-1-[(3-bromo-4,5-dihydro-isoxazol-5-ylmethyl)-carbamoyl]-ethyl}-carbamic acid benzyl ester (56) | $0.24 \times 10^{-3}$ | 0.54 | 2300 |
| [(S)-1-[(3-Bromo-4,5-dihydro-isoxazol-5-ylmethyl)-carbamoyl]-2-(1H-indol-3-yl)-ethyl]-carbamic acid benzyl ester (57) | $0.31 \times 10^{-3}$ | 0.78 | 2500 |
| {(S)-1-[(3-Bromo-4,5-dihydro-isoxazol-5-ylmethyl)-methyl-carbamoyl]-2-phenyl-ethyl}-carbamic acid benzyl ester (58) | $0.26 \times 10^{-3}$ | 0.19 | 730 |
| [(S)-1-[(3-Bromo-4,5-dihydro-isoxazol-5-ylmethyl)-methyl-carbamoyl]-2-(4-hydroxy-phenyl)-ethyl]-carbamic acid benzyl ester (59) | $0.42 \times 10^{-3}$ | 0.86 | 2000 |
| 1-(3-Bromo-4,5-dihydro-isoxazol-5-ylmethyl)-3-phenyl-urea (60) | $1.1 \times 10^{-3}$ | 0.89 | 810 |
| 1-(3-Bromo-4,5-dihydro-isoxazol-5-ylmethyl)-3-(2-chloro-5-trifluoromethyl-phenyl)-urea (61) | $0.91 \times 10^{-3}$ | 0.95 | 1000 |
| 1-(3-Bromo-4,5-dihydro-isoxazol-5-ylmethyl)-3-(4-chloro-2-trifluoromethyl-phenyl)-urea (62) | $1.3 \times 10^{-3}$ | 1.1 | 850 |
| 1-(3-Bromo-4,5-dihydro-isoxazol-5-ylmethyl)-3-(4-fluoro-phenyl)-urea (63) | $1.3 \times 10^{-3}$ | 1.0 | 770 |
| 1-(3-Bromo-4,5-dihydro-isoxazol-5-ylmethyl)-3-(2,5-dimethyl-phenyl)-urea (64) | $0.96 \times 10^{-3}$ | 0.97 | 1000 |

The above results demonstrate that the compounds tested have tTGase inhibitory activity.

Example 3

The following compounds were synthesized as additional examples of analogues of [(S)-1-[(3-Bromo-4,5-dihydro-isoxazol-5-ylmethyl)-methyl-carbamoyl]-2-(4-hydroxy-phenyl)-ethyl]-carbamic acid benzyl ester, for example as set forth in structure I of the present invention. Compounds reported below are specific examples of transglutaminase inhibitors of use to treat Celiac Sprue as well as other diseases associated with undesirable activity of transglutaminase.

TABLE 2

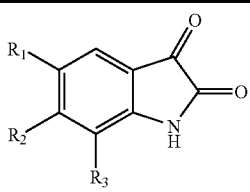

Tissue transglutaminase inhibition by Istatin derivatives

| Tested compound (R) | $K_1$ (M) |
|---|---|
| R1=R2=R3=H | $8.6 \times 10^{-4}$ |
| R2=R3=H, R1=NO$_2$ | $4.8 \times 10^{-5}$ |
| R2=R3=H; R1=I | $2.2 \times 10^{-5}$ |
| R2=R3=H; R1=F | $1.8 \times 10^{-5}$ |
| R1=R2=H; R3=Ph | $4 \times 10^{-4}$ |
| R1=R3=H; R2=Ph | $3.5 \times 10^{-4}$ |

TABLE 3

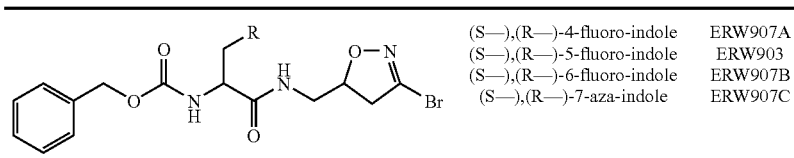

| R = | | kinh (/min) | KI (mM) | kinh/KI (/Mmin) |
|---|---|---|---|---|
| (S—),(R—)-4-fluoro-indole | ERW907A | | | <1200 |
| (S—),(R—)-5-fluoro-indole | ERW903 | | | >1200 |
| (S—),(R—)-6-fluoro-indole | ERW907B | | | <1200 |
| (S—),(R—)-7-aza-indole | ERW907C | | | <1200 |

TABLE 3-continued

| R = | | | kinh (/min) | KI (mM) | kinh/KI (/Mmin) |
|---|---|---|---|---|---|
| 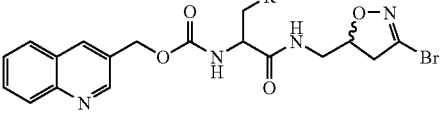 | (S—)-p-hydroxyphenyl | ERW1041A | 0.184 | 0.0631 | 2900 |
| | (S—),(R—)-5-hydroxy-indole | ERW1041B | 2.57 | 1.38 | 1850 |
| | (S—),(R—)-5-methoxy-indole | ERW1041D | 0.283 | 0.1725 | 1600 |
| | (S—)-5-fluoro-indole | ERW1069 | 0.1314 | 0.0049 | 26800 |
| 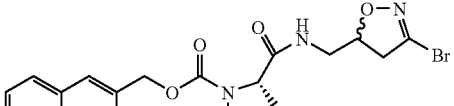 | | ERW1041E | 2.856 | 0.9527 | 3000 |
| 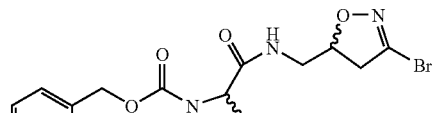 | | ERW1045 | | | <1200 |

The specific compounds that were synthesized are as follows:
ERW903 [1-[(3-Bromo-4,5-dihydro-isoxazol-5-ylmethyl)-carbamoyl]-2-(5-fluoro-1H-indol-3-yl)-ethyl]-carbamic acid benzyl ester (65)
ERW907A [1-[(3-Bromo-4,5-dihydro-isoxazol-5-ylmethyl)-carbamoyl]-2-(4-fluoro-1H-indol-3-yl)-ethyl]-carbamic acid benzyl ester (66)
ERW907B [1-[(3-Bromo-4,5-dihydro-isoxazol-5-ylmethyl)-carbamoyl]-2-(6-fluoro-1H-indol-3-yl)-ethyl]-carbamic acid benzyl ester (67)
ERW907C [1-[(3-Bromo-4,5-dihydro-isoxazol-5-ylmethyl)-carbamoyl]-2-(1H-pyrrolo[2,3-b]pyridin-3-yl)-ethyl]-carbamic acid benzyl ester (68)
ERW1041A [1-[(3-Bromo-4,5-dihydro-isoxazol-5-ylmethyl)-carbamoyl]-2-(4-hydroxy-phenyl)-ethyl]-carbamic acid quinolin-3-ylmethyl ester (69)
ERW1041B = [1-[(3-Bromo-4,5-dihydro-isoxazol-5-ylmethyl)-carbamoyl]-2-(5-hydroxy-1H-indol-3-yl)-ethyl]-carbamic acid quinolin-3-ylmethyl ester (70)
ERW1041D [1-[(3-Bromo-4,5-dihydro-isoxazol-5-ylmethyl)-carbamoyl]-2-(5-methoxy-1H-indol-3-yl)-ethyl]-carbamic acid quinolin-3-ylmethyl ester (71)
ERW1041E 2-[(3-Bromo-4,5-dihydro-isoxazol-5-ylmethyl)-carbamoyl]-pyrrolidine-1-carboxylic acid quinolin-3-ylmethyl ester (72)
ERW1045 2-[(3-Bromo-4,5-dihydro-isoxazol-5-ylmethyl)-carbamoyl]-2,3-dihydro-indole-1-carboxylic acid benzyl ester (73)
ERW1069 [1-[(3-Bromo-4,5-dihydro-isoxazol-5-ylmethyl)-carbamoyl]-2-(5-fluoro-1H-indol-3-yl)-ethyl]-carbamic acid quinolin-3-ylmethyl ester (74)

Synthesis of compounds ERW903, 907A, B, and C and 1045 were synthesized using the methods of Choi et al, *Chemistry & Biology*, Volume 12, Issue 4, Pages 469-475.

Synthesis of compounds ERW1041 A, B, C, D, E, and 1069 were synthesized using the methods of Choi et al. *Chemistry & Biology*, Volume 12, Issue 4, Pages 469-475, except the amino-acid amines are protected by a quinoline-containing carbamate. This quinoline-containing carbamate is synthesized by reducing 3-quinolylcarbaldehyde with sodium borohydride in THF followed by an aqueous workup and flash chromatography yielding 3-quinolylcarbinol. para-Nitrophenylchloroformate is reacted with 3-quinolylcarbinol in methylene chloride and N-methyl morpholine to give a carbonate of 3-quinoline methanol and para-Nitro-phenol. After purification by flash chromatography, this carbonate is reacted with the methyl ester of the amino acid in neat DMF to give the named compounds.

Example 4

Use of tTGase Inhibitors for Treating Neurologic Cancers

Preliminary pharmacokinetic and pharmacodynamic studies in mice on a prototype inhibitor, KCC009 ((S)-[3-(4-hydroxyphenyl)-2-N-(phenylmethyloxycarbonyl)aminopropanoic acid N-(3'-bromo-4',5'-dihydro-5'-isoxalyl)methylamide) (59), suggested that the compound had reasonable oral bioavailability, a short serum half-life, efficient TG2 inhibition in small intestinal tissue, and low toxicity. In vitro treatment of glioblastoma cells with KCC009 promoted apoptosis and enhanced sensitivity to chemotherapeutic agents. Such treatment also resulted in changes in levels of proteins altered in glioblastomas that enhance survival and are involved with promoting resistance to chemotherapy and radiation therapy. These changes in proteins included markedly decreased levels of phosphorylated Akt, survivin, phosphorylated Bad, and phosphorylated glycogen synthetase kinase 3β; and increased levels of the pro-apoptotic BH3-only protein, Bim. In vivo studies with subcutaneous murine DBT glioblastoma tumors revealed that KCC009 showed excellent synergism with N,N-bis(2-chloroethyl)-N-nitrosourea (BCNU, carmustine). Together, these findings warranted further investigation into the use of KCC009 for treating neuro-oncological diseases.

To test whether therapeutic doses of KCC009 can modulate TG2 activity associated with intracranial glioblastomas, DBT tumors were injected intracranially in mice. As judged by MRI, the mice consistently established intracranial tumors after 7-10 days following injections, which, if untreated, caused death by 2-3 weeks. In an initial dose-finding experiment, cohorts of mice were administered 4 daily doses of vehicle or KCC009 (12.5 mg/kg, 25 mg/kg and 50 mg/kg) starting on day 11 after intra-cranial injections. Twenty-four hours later, the mice were sacrificed and tumors analyzed. Grossly tumor dissections revealed that control mouse brains had the largest tumors, and their contra-lateral hemispheres were either swollen or infiltrated with microscopic tumor cells. Mice that received 12.5 mg/kg or 25 mg/kg doses had smaller tumors and reduced brain swelling. One mouse for the 50 mg/kg dose did not have any gross tumor. Based on these findings a dose of 35 mg/kg was used for subsequent experiments in mice harboring intracranial DBT tumors.

To evaluate the activity of KCC009 as a chemosensitizer, mice harboring DBT tumors were treated either with 10 mg/kg BCNU alone (2 mice) or BCNU+35 mg/kg KCC009 (3 mice). As before, 4 daily drug doses were administered intraperitoneally starting on day 11. Tumors were harvested for immuno-histological analysis 24 h after the last dose. As seen in FIG. 1, tumors from KCC009-treated animals showed a decrease in fibronectin staining overall and an apparent dramatic decrease in the extracellular matrix. The controls showed linear strands of fibronectin in the ECM while the KCC009 groups had clumps of intracellular fibronectin.

To verify that the observed differences between BCNU versus BCNU+KCC009 treated mice were due to inhibition of tumor associated TG2, mice treated with four daily doses of BCNU alone or BCNU+50 mg/kg KCC009 were sacrificed either 15 min or 24 h after the last dose, and tumor associated TG2 activity was measured. As summarized in Table 4, KCC009 treatment led to significant suppression of TG2 activity after 15 min, whereas enzyme activity recovers fully by 24 h. Both uninhibited and inhibited activity levels are consistent with similar measurements in the small intestinal mucosa (data not shown).

TABLE 4

Inhibition of intracranial tumor associated TG2 by KCC009.

| Time after drug dose | TG2 activity-BCNU alone (nmol/h/mg protein) | TG2 activity-BCNU + KCC009 (nmol/h/mg protein) |
|---|---|---|
| 15 min | 2.1 ± 0.2 (n = 4) | 1.2 ± 0.3 (n = 4) |
| 24 h | 2.2 ± 0.3 (n = 2) | 2.1 ± 0.2 (n = 3) |

Figure 2:
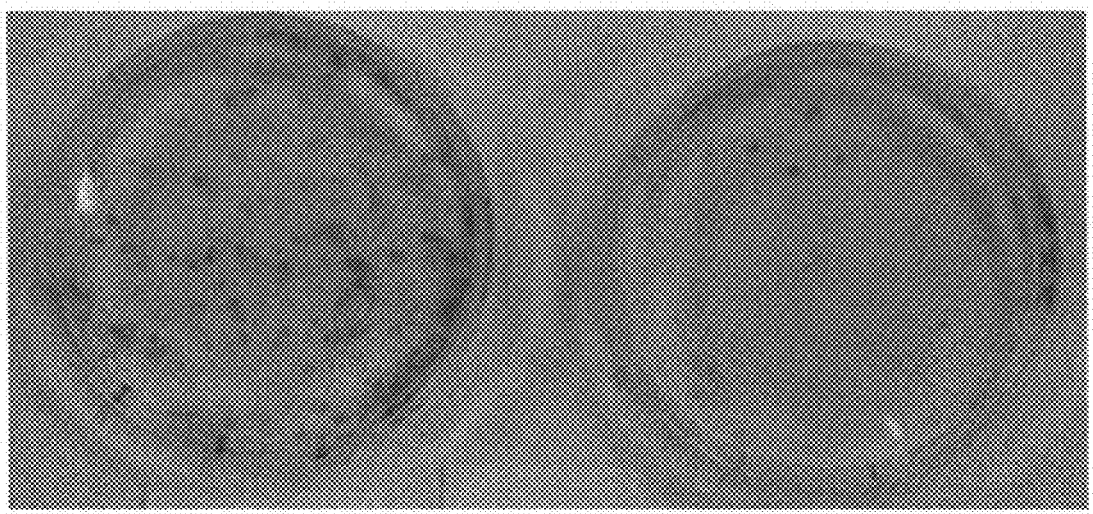
FIG. 2: KCC009 as a radiosensitizer. Cultured DBT cells were treated with radiation alone (3.2 Gy) (left) or radiation plus 0.5 mM KCC009 (right), and plated on soft agar to evaluate cell viability. At corresponding concentrations, KCC009 alone does not affect cell viability.

In addition to evaluating the chemosensitizing potential of KCC009, this compound's potential as a radiosensitizer was also evaluated. For this clonogenic assays were used to measure colony formation after a single radiation treatment. The studies were performed in triplicate with varying doses of XRT and number of cells plated. In brief, treatment of DBT cells in culture with 0.5 mM KCC009 enhanced cell death in response to 3.2 Gy of X-ray radiation by two orders of magnitude. A representative photo of a clonogenic assay plate treated with X-ray alone compared with a plate pre-treated with 0.5 mM KCC009 plus X-ray is shown in FIG. 2.

Figure 3:
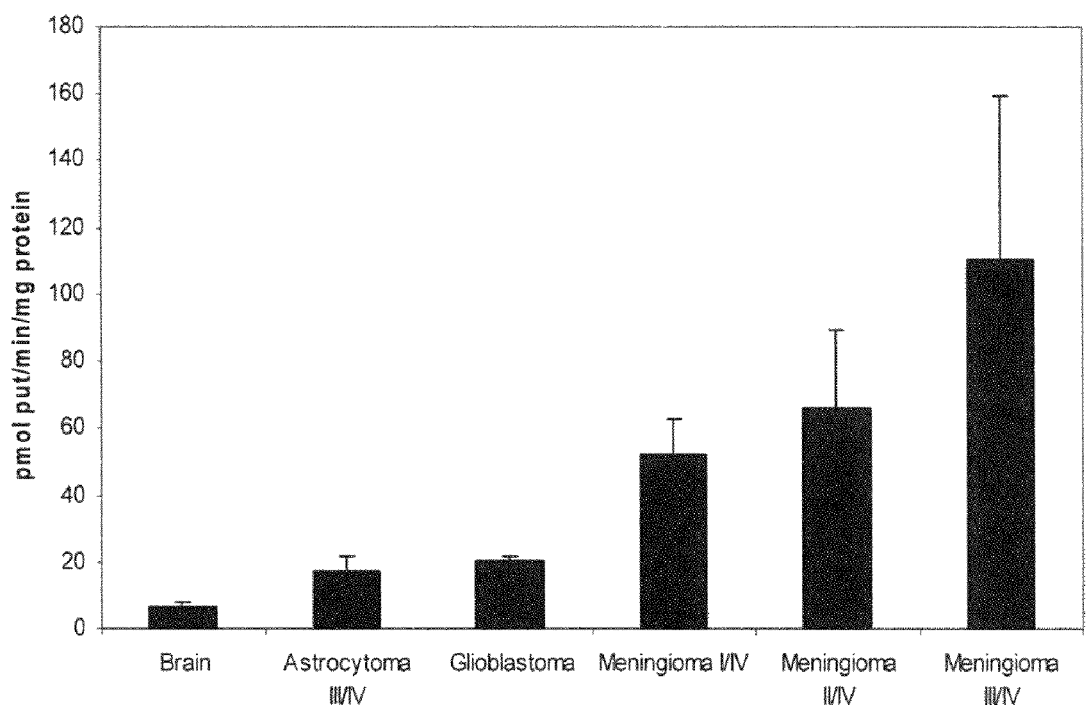
FIG. 3: TG2 activities of the 30 brain tumors and 4 non-malignant brain tissue samples

To highlight the clinical relevance of TG2 inhibition among tumors of neurological origin, TG2 activity was assessed in tissue samples from astrocytomas (Grade III/IV and IV/IV) and meningiomas (Grades I/IV; II/IV; and III/IV). TG2 activity was measured from 50 µM thick sections of brain tumor specimens collected from the operating room. Each specimen was coded and stored in the Tumor Repository. Samples analyzed included 4 normal brain sample, 6 anaplastic astrocytomas (Grade III/IV); 9 glioblastomas (Grade III/IV), 7 typical meningiomas (Grade I/IV); 5 atypical meningiomas (Grade II/IV); and 3 anaplastic meningiomas (Grade III/IV). The results in FIG. 3 show that astrocytomas, glioblastomas and especially meningiomas had elevated TG2 activity and are therefore candidates for KCC009 therapy.

Figure 4:
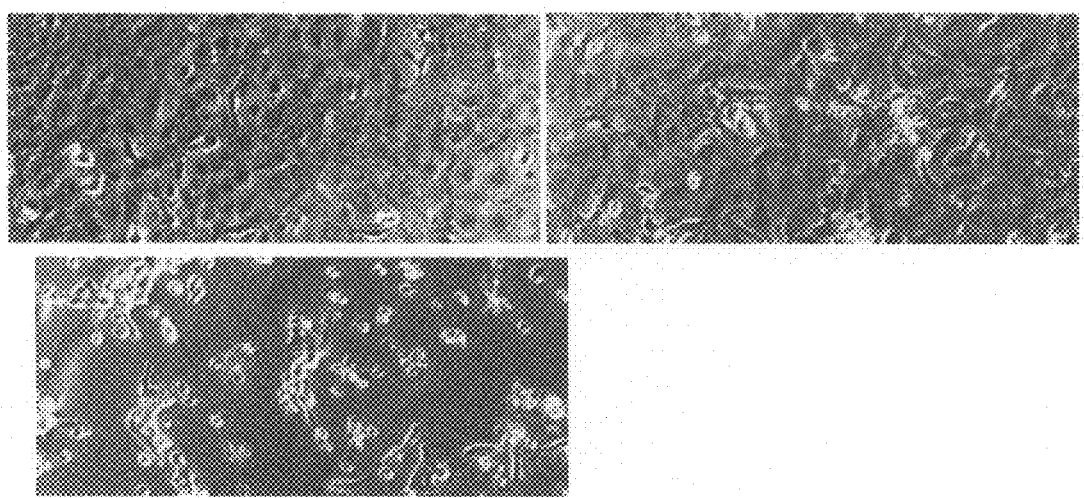
FIG. 4: Top left: control IOMM meningioma cells; Top right: IOMM cells exposed to 20 Gy radiation; Bottom left: IOMM cells exposed to 0.5 mM KCC009 and 20 Gy radiation.
Figure 5:
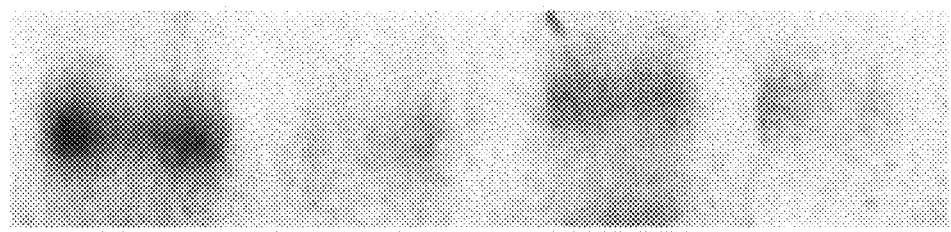
FIG. 5: Western blot analysis of lysates from IOMM cells treated with KCC009 and/or BCNU. Lysates were immunoprecipitated with anti-fibronectin antibodies, and the Western blots were probed with anti-TG2 antibodies. Lanes (left to right): Control, KCC009 only, BCNU only, KCC009+BCNU. KCC009 and BCNU were used at concentrations of 0.5 mM and 6.25 µM, respectively. Disappearance of TG2 from lanes treated with KCC009 illustrates loss of association of TG2 with the extracellular matrix.

To verify the therapeutic utility of KCC009 against meningiomas, IOMM-Lee meningioma cells were treated with 20 Gy of radiation with and without KCC009. As shown in FIG. 4, KCC009 dramatically sensitized meningioma cells to radiation. Similar data was also obtained when KCC009 was used in combination with BCNU. To demonstrate the relationship between TG2 inhibition and extracellular matrix assembly, immunoprecipitated fibronectin from the different cultures were stained with anti-TG2 antibodies via Western blot analysis. As seen in FIG. 5, cells treated with KCC009 showed a loss of association between TG2 and fibronectin.

Figure 6:
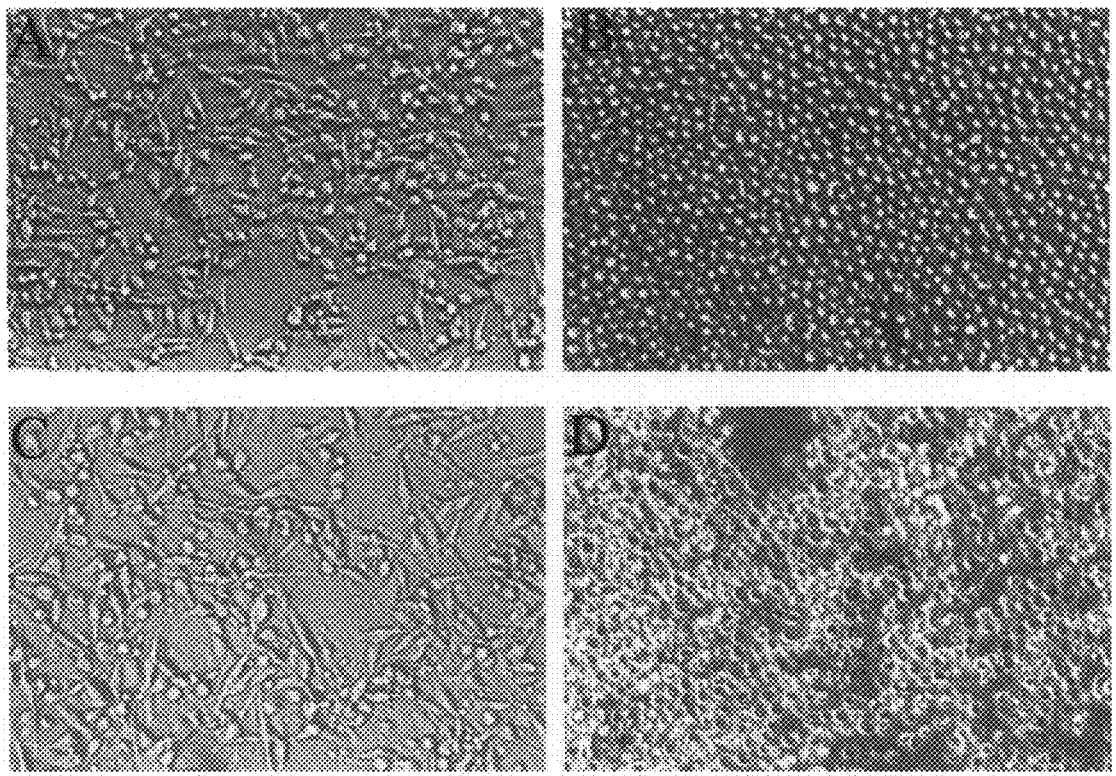
FIG. 6A-6D: Photomicrographs of B16 (mouse melanoma cells) after 24 h treatment with KCC009 and/or BCNU. A) Control; B) 1 mM KCC009 only; C) 6.25 µM BCNU only; D) KCC009+BCNU combination.

Activity of KCC009 against melanomas: Melanomas are cancers of the neural crest-derived cells that provide pigmentation to skin and other tissues. No current treatments substantially enhance patient survival once metastasis has occurred. As shown in FIG. 6, B16 mouse melanoma cells are sensitive to KCC009 alone and especially KCC009 and BCNU.

To demonstrate the utility of KCC009 in cancer in combination with other chemotherapeutic agents, HCT-116, a human colon cancer cell line, was treated with epothilone C (a member of a promising class of anti-mitotic agents) and/or KCC009. Incubation of HCT-116 with increasing levels of KCC009 in the 1-100 µM range reduced the $GI_{50}$ for epothilone C by >2-fold.

Example 5

Figure 7:
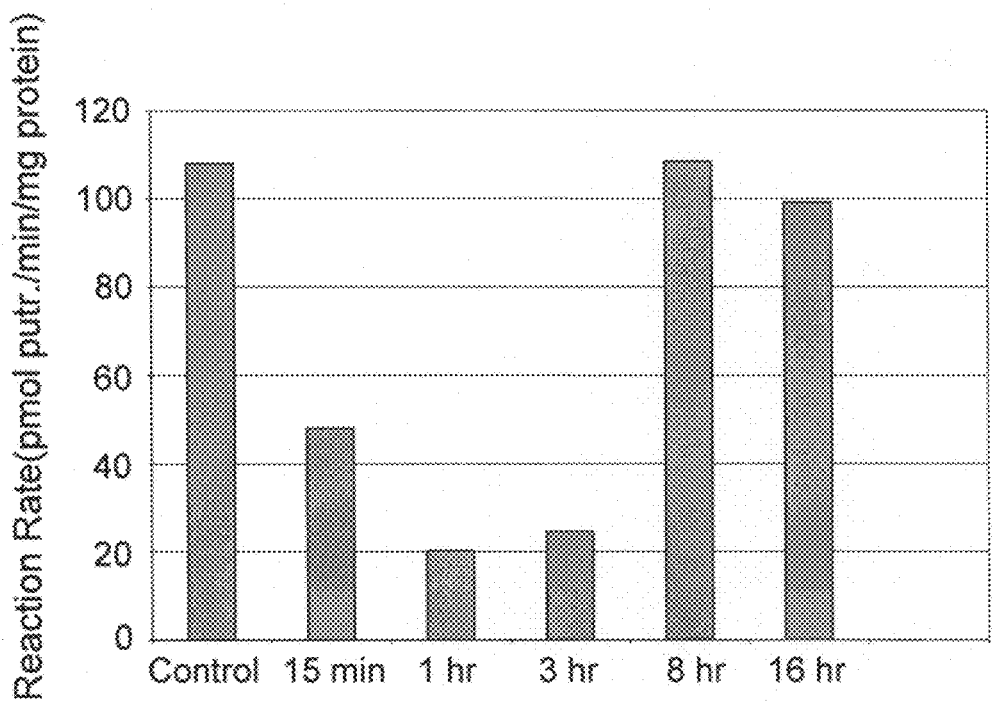
FIG. 7: Time dependent inhibition of small intestine mucosal TG2 in mice dosed intra-peritoneally with 60 mg/kg KCC009. Mice were sacrificed at different times, intestinal mucosa were harvested and assayed for TG2 activity. The activity of TG2 in jejunal tissue from TG2-knockout mice is <5% of the observed wild-type levels, suggesting the assay employed by us is adequately specific for TG2 activity.

Due to the absence of an appropriate animal model for Celiac Sprue, the therapeutic benefit of TG2 inhibitors for this disease can only be validated in patients. Our goal is therefore to identify a safe, oral TG2 inhibitor that can block mucosal TG2 activity in the upper small intestine of Celiac Sprue patients. Such an agent could be used in the context of a short (2 week) blinded crossover trial in Celiac Sprue patients to determine if TG2 inhibition protects a Celiac Sprue patient from gluten-induced malabsorption. From available data, KCC009 may be precisely such a compound. As shown in FIG. 7, intra-peritoneal administration of KCC009 results in strong inhibition of TG2 activity in mice on a short timescale (~1 h), but this activity recovers completely within 8 h. To test whether orally administered KCC009 can inhibit jejunal TG2 activity, adult male rats were dosed with 35 mg/kg KCC009 in a kneaded gluten vehicle. Animals were sacrificed 1 h after administration of either vehicle-gluten (n=3) or drug-gluten (n=4), and jejunal mucosa was harvested. In vehicle treated animals, jejunal TG2 activity was 21±7 pmol/min/mg protein, whereas in KCC009 treated rats TG2 activity of 5.5±3 pmol/min/mg protein was observed. Thus, a suitable oral formulation may therefore enable local delivery of KCC009 to intestinal mucosa.

Example 6

Preparation and Evaluation of Enantiopure Dihydroxyisoxazole Containing tTGase Inhibitors Enantiopure dihydroisoxazole moieties were synthesized as per Choi et al. *Chemistry & Biology*, Volume 12, Issue 4, Pages 469-475 with the following exceptions. The 3+2 dipolar cycloaddition forming the dihydroisoxazole was performed with allyl alcohol rather than allylamine. The racemic dihydroisoxazole-containing alcohol product was acetylated by treatment with Amano Lipase PS-C in vinyl acetate, and purified by flash chromatography. Retreating the acetylated racemates with Amano Lipase PS in water/methanol resolved the two enantiomers. The lipase hydrolyzed the (R)(−) enantiomer, leaving the (S-)(+) enantiomer acetylated. Separation and purification by column chromatography cleanly yielded the two compounds. The (S-)(+) enantiomer was hydrolyzed with lithium hydroxide in methanol/water. The optical rotations of the two enantiomers were in very good agreement with literature values. (R-) $\alpha_D$=−130° (lit value −141°); (S-) $\alpha_D$=+130°(lit value +141°).

The two compounds: [1-[(3-Bromo-4,5-dihydro-isoxazol-(R-)-5-ylmethyl)-carbamoyl]-2-(1H-indol-3-yl)-ethyl]-carbamic acid naphthalen-2-ylmethyl ester (ERW1095D) and [1-[(3-Bromo-4,5-dihydro-isoxazol-(S-)-5-ylmethyl)-carbamoyl]-2-(1H-indol-3-yl)-ethyl]-carbamic acid naphthalen-2-ylmethyl ester (ERW1095C) were synthesized by the method of Choi et al. *Chemistry & Biology*, Volume 12, Issue 4, Pages 469-475 from naphthalene-2-methanol, L-tryptophan methyl ester and the two enantiopure alcohols.

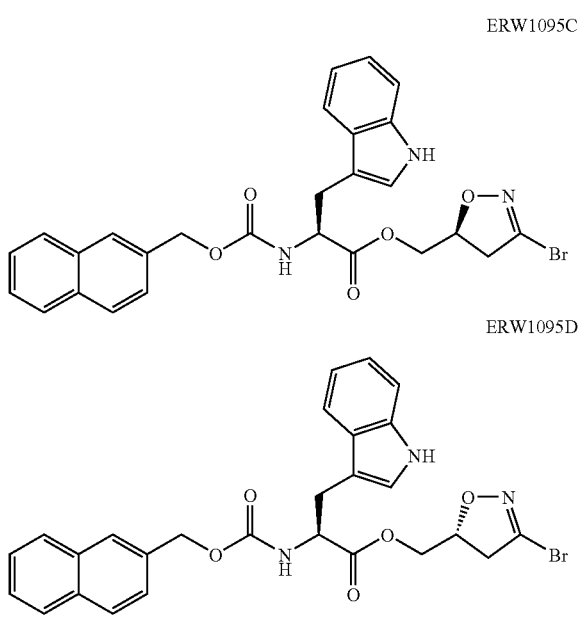

ERW1095C

ERW1095D

The two compounds were assayed for tTG2 inhibition activity in vitro as per Choi et al. Both compounds exhibited tTG2 inhibition. Gross observation of reaction progress in the presence and absence of the 2 inhibitors showed the compound containing the (R-) dihydroisoxazole moiety to be a greater inhibitor of tTG2 than its (S-) dihydroisoxazole diastereomer.

Experiments by Choi et al indicate esters of the type ERW1095, in general, are distinctly poorer tTG2 inhibitors than their corresponding amides. The amide versions of these enantiopure esters will be synthesized from the enantiopure alcoholic dihydroisoxazoles above. The alcohols will be converted to amines by means of Mitsunobu-like reaction conditions. The alcohols may be treated with DEAD or DIAD followed by triphenylphosphine followed by hydrazine. The chemical literature contains many dozens of examples of alcohol-to-amine conversions using variants of these reaction conditions. Possessing the enantiopure amines reduces synthesis of the enantiopure amides to a straightforward use of techniques detailed in Choi et al.

A second approach to synthesizing the enantiopure amides is the synthesis of the previously discussed allylamine-derived dihydroisoxazole followed by chiral resolution of the racemic product with penicilin acylase via variants of the methods of Waldmann et al. *Chem. Commun.*, 1997, 1861; *Angew. Chem., Int. Ed. Engl.*, 1997, 36, 647 and *J. Am. Chem. Soc.*, 1997, 38, 6702.

A third approach to enantiopure amide versions of these compounds is from resolution of chiral mandelic acid amides of the amine dihydroisoxazoles after the method of Castelhano et al., *Bioorg. Chem.* (1988) 16, 335-340.

Example 7

Synthesis and Evaluation of Ac-Pro-DON-Leu-Pro-Phe-NH$_2$ (DON=6-diazo-5-oxo-norleucine)

Earlier disclosures had reported the synthesis and evaluation of a promising peptidic inhibitor of human TG2, (SEQ ID NO:1) Ac-Pro-Gln-Pro-DON-Leu-Pro-Phe-NH$_2$. We now disclose a truncated analog that is easier to synthesize and has greater activity.

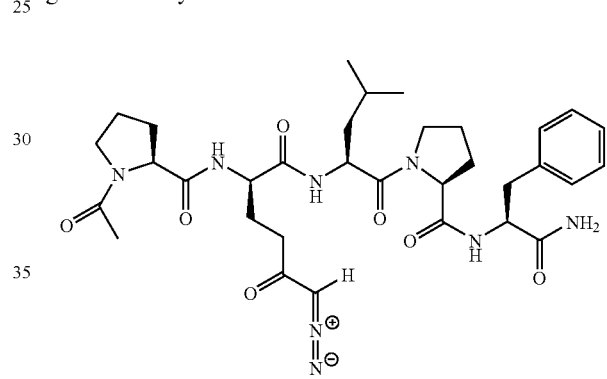

$C_{33}H_{46}N_8O_7$
Exact Mass: 666.35
Mol. Wt.: 666.77
m/e: 666.35 (100.0%), 667.35 (38.9%), 668.36 (6.5%), 668.35 (2.5%), 669.36 (1.3%) C, 59.44; H, 6.95; N, 16.81; O, 16.80

Synthesis: (SEQ ID NO:2) Ac-PELPF-NH$_2$ was synthesized using standard Boc chemistry solid phase peptide and dried over KOH. 30 mg (46.8 μmol) (SEQ ID NO:2) Ac-PELPF-NH$_2$ was dissolved in 4 ml of dry THF and cooled in an ice bath. 8.2 μl (1.6 eq) of 4-Methylmorpholine was added followed by 7.3 μl (1.2 eq) of Isobutyl chloroformate and allowed to react for 5 minutes (adapted from Hausch et al., *Chem. Biol.* (2003) 10, 225-231). The reaction mixture was added dropwise to a saturated solution of Diazomethane in 20 ml of dry Diethyl ether which was prechilled in an ice bath. The solution was allowed to react for 30 min on ice followed by 30 min at room temperature. The solvent was removed by evaporation and the residue was purified by high pressure liquid chromatography (C18, water/acetonitrile+0.1 M Triethylammonium bicarbonate gradient).

Characterization: (SEQ ID NO:3) Ac-Pro-DON-Leu-Pro-Phe-NH$_2$ was characterized by the method of Hausch et al. (Hausch et al., *Chem. Biol.* (2003) 10, 225-231). $K_i$=60 nM, $k_i$=0.5 min$^{-1}$, $k_i/K_i$=8.3 μM min$^{-1}$.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A pharmaceutical formulation comprising a tTGase inhibitor of the formula:

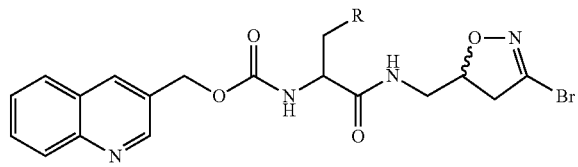

wherein R is a substituted or unsubstituted heteroaryl; and a pharmaceutically acceptable excipient for oral or injectable delivery.

2. The formulation of claim 1, wherein said tTGase inhibitor is [1-[(3-Bromo-4,5-dihydro-isoxazol-5-ylmethyl)-carbamoyl]-2-(5-fluoro-1H-indol-3-yl)-ethyl]-carbamic acid quinolin-3-ylmethyl ester.

3. The formulation of claim 1, wherein the formulation is an oral formulation.

4. The formulation of claim 3, wherein said oral formulation comprises an enteric coating.

5. The formulation of claim 3, wherein said oral formulation comprises engineered polymer microspheres made of biologically erodable polymers.

6. The formulation of claim 1, wherein the effective dose is 0.01 mg to 500 mg V/kg body weight per day.

7. The formulation of claim 1, wherein said tTGase inhibitor is admixed with food.

* * * * *